(12) United States Patent
Barolat

(10) Patent No.: US 8,549,015 B2
(45) Date of Patent: Oct. 1, 2013

(54) METHOD AND SYSTEM FOR DISTINGUISHING NOCICEPTIVE PAIN FROM NEUROPATHIC PAIN

(76) Inventor: Giancarlo Barolat, Golden, CO (US)

( * ) Notice: Subject to any disclaimer, the term of this patent is extended or adjusted under 35 U.S.C. 154(b) by 0 days.

(21) Appl. No.: 13/288,409

(22) Filed: Nov. 3, 2011

(65) Prior Publication Data

US 2012/0290216 A1   Nov. 15, 2012

Related U.S. Application Data

(63) Continuation of application No. 12/102,322, filed on Apr. 14, 2008, now abandoned.

(60) Provisional application No. 60/915,295, filed on May 1, 2007.

(51) Int. Cl.
*G06F 17/30* (2006.01)

(52) U.S. Cl.
USPC ............................ 707/748; 707/603; 705/7.32

(58) Field of Classification Search
USPC ................. 707/600, 603, 607, 705, 708, 721, 707/723, 748, 749, 754, 758, 941, 999.107; 705/1.1, 2, 3, 7.32
See application file for complete search history.

(56) References Cited

U.S. PATENT DOCUMENTS

| | | |
|---|---|---|
| 1,597,061 A | 8/1926 | Cultra |
| 3,195,540 A | 7/1965 | Waller |
| 3,646,940 A | 3/1972 | Timm et al. |
| 3,724,467 A | 4/1973 | Avery et al. |
| 3,796,221 A | 3/1974 | Hagfors |
| 3,822,708 A | 7/1974 | Zilber |
| 3,893,463 A | 7/1975 | Williams |
| 4,024,875 A | 5/1977 | Putzke |
| 4,219,027 A | 8/1980 | Frosch et al. |
| 4,232,679 A | 11/1980 | Schulman |
| 4,315,503 A | 2/1982 | Ryaby et al. |
| 4,379,462 A | 4/1983 | Borkan et al. |
| 4,441,498 A | 4/1984 | Nordling |
| 4,459,989 A | 7/1984 | Borkan |
| 4,549,556 A | 10/1985 | Tarjan et al. |
| 4,608,985 A | 9/1986 | Crish et al. |
| 4,934,368 A | 6/1990 | Lynch |
| 5,095,905 A | 3/1992 | Klepinski |

(Continued)

OTHER PUBLICATIONS

Freynhagen et al., PainDETECT: a new screening questionaire to identify neuropathic components in patients with back pain, Current Mediacl Research and Opinion, vol. 22, No. 10, 2006, pp. 1911-1920, LibraPharm Limited.*

(Continued)

*Primary Examiner* — Greta Robinson
(74) *Attorney, Agent, or Firm* — Haynes and Boone, LLP

(57) ABSTRACT

A method of distinguishing nociceptive pain from neuropathic pain includes providing a series of questions for answering by the patient. Each of the answers by the patient are given a numerical value within a nociceptive pain category and a neuropathic pain category. The values within the two categories are then summed, with the resultants potentially modified using a series of one or more equations. The ratio of the neuropathic pain to the nociceptive pain is then calculated. The ratio provides a value for the physician to diagnose the patient as suffering from nociceptive pain, neuropathic pain, or both nociceptive pain and neuropathic pain. Embodiments of the present invention include a system for assisting a physician to identify whether a patient's pain is nociceptive pain or neuropathic pain.

18 Claims, 17 Drawing Sheets

(56) References Cited

U.S. PATENT DOCUMENTS

| | | |
|---|---|---|
| 5,121,754 A | 6/1992 | Mullett |
| 5,282,468 A | 2/1994 | Klepinski |
| 5,318,572 A | 6/1994 | Helland et al. |
| 5,324,324 A | 6/1994 | Vachon et al. |
| 5,330,515 A | 7/1994 | Rutecki et al. |
| 5,376,103 A | 12/1994 | Anderson et al. |
| 5,417,719 A | 5/1995 | Hull et al. |
| 5,501,703 A | 3/1996 | Holsheimer et al. |
| 5,514,175 A | 5/1996 | Kim et al. |
| 5,522,874 A | 6/1996 | Gates |
| 5,571,118 A | 11/1996 | Boutos |
| 5,643,330 A | 7/1997 | Holsheimer et al. |
| 5,797,923 A | 8/1998 | Aiyar et al. |
| 5,895,416 A | 4/1999 | Barreras et al. |
| 5,938,690 A | 8/1999 | Law et al. |
| 5,948,007 A | 9/1999 | Starkebaum et al. |
| 5,957,958 A | 9/1999 | Schulman et al. |
| 6,002,964 A | 12/1999 | Feler et al. |
| 6,027,456 A | 2/2000 | Feler et al. |
| 6,104,957 A | 8/2000 | Alo et al. |
| 6,224,549 B1 | 5/2001 | Drongelen |
| 6,246,912 B1 | 6/2001 | Sluijter et al. |
| 6,314,325 B1 | 11/2001 | Fitz |
| 6,345,199 B1 | 2/2002 | Thong |
| 6,386,685 B1 | 5/2002 | Sligioka |
| 6,421,566 B1 | 7/2002 | Holsheimer |
| 6,438,423 B1 | 8/2002 | Rezai et al. |
| 6,510,332 B1 | 1/2003 | Greenstein |
| 6,516,227 B1 | 2/2003 | Meadows et al. |
| 6,553,263 B1 | 4/2003 | Meadows et al. |
| 6,609,031 B1 | 8/2003 | Law et al. |
| 6,675,046 B2 | 1/2004 | Holsheimer |
| 6,697,676 B2 | 2/2004 | Dahl et al. |
| 6,735,472 B2 | 5/2004 | Helland |
| 6,795,737 B2 | 9/2004 | Gielen et al. |
| 6,885,888 B2 | 4/2005 | Rezai |
| 6,892,097 B2 | 5/2005 | Holsheimer |
| 6,895,280 B2 | 5/2005 | Meadows et al. |
| 6,928,320 B2 | 8/2005 | King |
| 6,941,171 B2 | 9/2005 | Mann et al. |
| 6,944,507 B2 | 9/2005 | Froberg et al. |
| 6,999,819 B2 | 2/2006 | Swoyer et al. |
| 6,999,820 B2 | 2/2006 | Jordan |
| 7,079,900 B2 | 7/2006 | Greenburg et al. |
| 7,099,718 B1 | 8/2006 | Thacker et al. |
| 7,107,097 B2 | 9/2006 | Stern et al. |
| 7,107,104 B2 | 9/2006 | Keravel et al. |
| 2001/0037222 A1 | 11/2001 | Platt et al. |
| 2002/0111661 A1 | 8/2002 | Cross et al. |
| 2003/0078633 A1 | 4/2003 | Firlik et al. |
| 2003/0140063 A1 | 7/2003 | Pizzorno et al. |
| 2003/0153959 A1 | 8/2003 | Thacker et al. |
| 2003/0204415 A1 | 10/2003 | Knowlton |
| 2004/0093093 A1 | 5/2004 | Andrews |
| 2004/0127953 A1 | 7/2004 | Kilgore et al. |
| 2004/0167584 A1 | 8/2004 | Carroll et al. |
| 2004/0260310 A1 | 12/2004 | Harris |
| 2005/0010259 A1 | 1/2005 | Gerber |
| 2005/0055065 A1 | 3/2005 | Campbell |
| 2005/0055779 A1 | 3/2005 | Damewood |
| 2005/0065394 A1 | 3/2005 | Spiegel |
| 2005/0070982 A1 | 3/2005 | Heruth et al. |
| 2005/0107841 A1 | 5/2005 | Meadows et al. |
| 2005/0119713 A1 | 6/2005 | Whitehurst et al. |
| 2005/0148149 A1 | 7/2005 | Nabeshima |
| 2005/0149148 A1 | 7/2005 | King |
| 2005/0182470 A1 | 8/2005 | Cross |
| 2005/0192644 A1 | 9/2005 | Boveja et al. |
| 2005/0228451 A1 | 10/2005 | Jaax et al. |
| 2005/0240242 A1 | 10/2005 | DiLorenzo |
| 2005/0240243 A1 | 10/2005 | Barolat et al. |
| 2006/0052826 A1 | 3/2006 | Kim et al. |
| 2006/0052836 A1 | 3/2006 | Kim et al. |
| 2006/0074450 A1 | 4/2006 | Boveja et al. |
| 2006/0100909 A1 | 5/2006 | Glimp et al. |
| 2006/0136008 A1 | 6/2006 | Tadlock |
| 2006/0147510 A1* | 7/2006 | Galer .......................... 424/449 |
| 2006/0178718 A1 | 8/2006 | Jordan |
| 2007/0271298 A1 | 11/2007 | Hang et al. |
| 2008/0058876 A1 | 3/2008 | Barolat |
| 2008/0132970 A1 | 6/2008 | Barolat |
| 2008/0183500 A1 | 7/2008 | Banigan |

OTHER PUBLICATIONS

Krause et al., Development of Neuropathic Pain Questionaire, The Clinical Journal of Pain, vol. 19, 2003, pp. 306-314, Lippincott Williams 8. Wilkins, Inc., Philadelphia, Pennsylvania.*

Disorbio et al., "Assessment and Treatment of Chronic Pain", Mar. 2006, Practical Pain Management, PPM Communications, Inc., pp. 1-10☐.

Lubenow et al., "Advances in Neurostimulation Systems Video Presentation", International Research Foundation for RSD/CRPS, Jul. 16, 2006, 12 pages☐.

Swan, "The Nervous System", Jim Swan, revised Oct. 26, 2005, 97 pages.

Bennett, "The LANSS Pain Scale: the Leeds assessment of neuropathic symptoms and signs", PAIN, vol. 92, 2001, pp. 147-157, International Association for the Study of Pain, Elsevier Science B.V., Amsterdam, The Netherlands.

Bennett et al., "Using screening tools to identify neuropathic pain", PAIN, vol. 127, 2007, pp. 199-203, International Association for the Study of Pain, Elsevier Science B.V., Amsterdam, The Netherlands.

Freynhagen et al., "PainDETECT: a new screening questionnaire to identify neuropathic components in patients with back pain", Current Medical Research and Opinion. vol. 22, No. 10, 2006, pp. 1911-1920, LibraPharm Limited.

"The Neuropathic Pain Scale", 1997, Galer-Jensen, "The Neuropathic Pain Scale", 1997, Lyon France.

Gilron et al., 'Neuropathic pain: a practical guide for the clinician, CMAJ, Aug. 1, 2006, vol. 175 (3), pp. 265-275, Canadian Medical Association, Ontario, Canada.

Jensen et al., Translation of symptoms and signs into mechanisms in neuropathic pain' PAIN, vol. 102, 2003, pp. 1-8, International Association for the Study of Pain, Elsevier Science B.V., Amsterdam, The Netherlands.

Krause et al., "Development of a Neuropathic Pain Questionnaire", The Clinical Journal of Pain, vol. 19, 2003, pp. 306-314, Lippincott Williams 8. Wilkins, Inc., Philadelphia, Pennsylvania.

"PainDetect Questionnaire", 2005, Pfizer Pharma GmbH.

Rasmussen et al., "Symptoms and signs in pabents with suspected neuropathic pain", PAIN, vol. 110, 2004, pp. 461-469, International Association for the Study of Pain, Elsevier Science B.V., Amsterdam, The Netherlands.

* cited by examiner

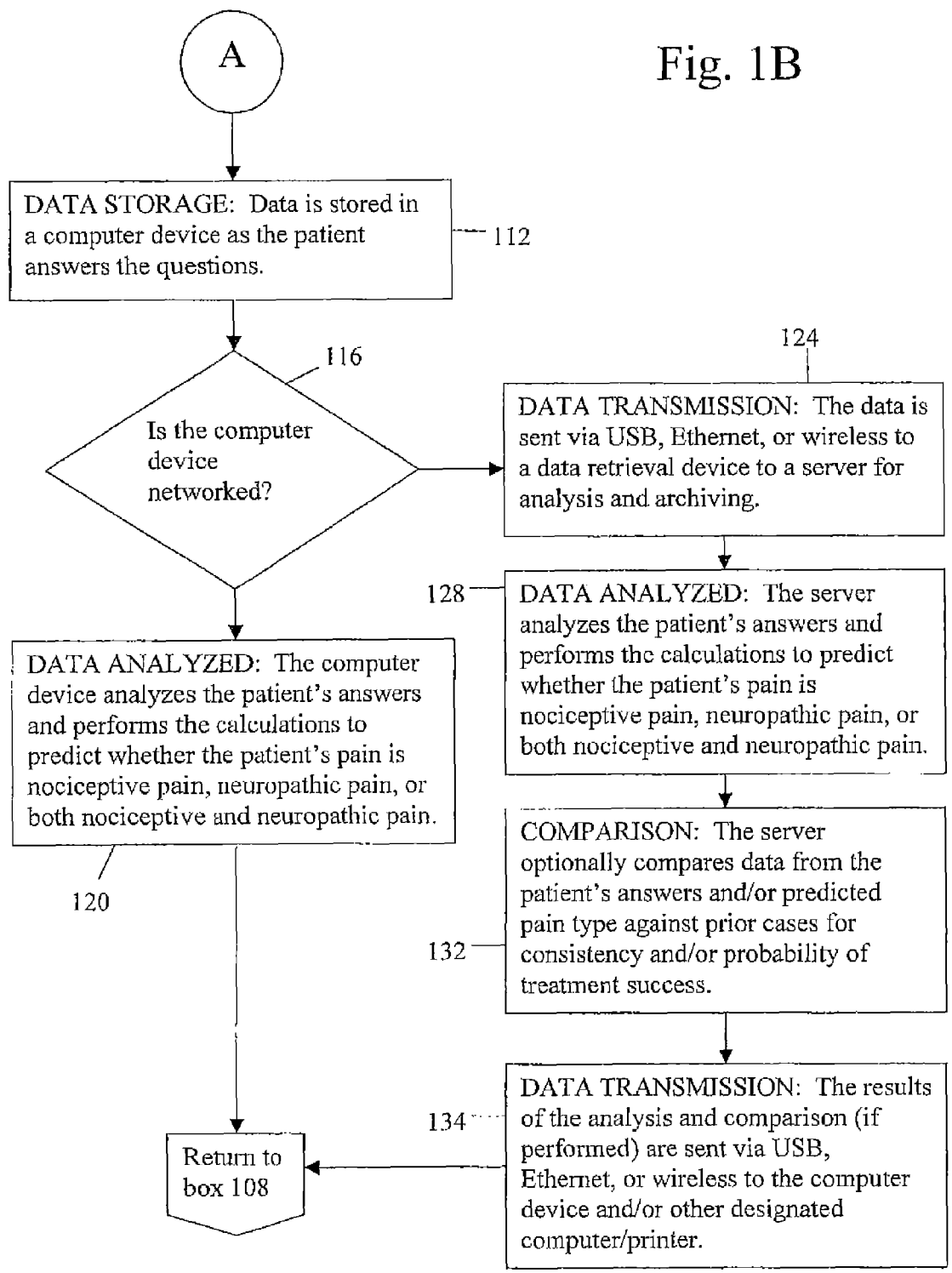

GENERAL QUESTIONS FOR ALL PATIENTS

| Question Designation 204 | Question 200 | Answer Designation 212 | Answer 208 | Nociceptive Pain Category 216 | Neuropathic Pain Category 220 |
|---|---|---|---|---|---|
| S1Q1 | How frequent is your pain? | a | Constant | 1 | 4 |
| | | b | Not constant; every day frequently | 3 | 3 |
| | | c | Not constant; every day infrequently | 4 | 1 |
| | | d | Not constant; not every day | 4 | 0 |
| S1Q2 | How long have you had the pain? | a | Less than a month | 1 | 0 |
| | | b | 1-6 months | 3 | 2 |
| | | c | 6-12 months | 2 | 3 |
| | | d | More than one year | 1 | 4 |
| S1Q3 | How bad is the pain? (at its worst) | a | Excruciating | 4 | 4 |
| | | b | Severe | 3 | 3 |
| | | c | Moderate | 2 | 1 |
| | | d | Mild | 0 | 0 |
| S1Q4 | How bad is the pain? (at its least) | a | Excruciating | 0 | 4 |
| | | b | Severe | 1 | 3 |
| | | c | Moderate | 2 | 1 |
| | | d | Mild | 4 | 1 |
| S1Q5 | About burning pain, which one applies to you? | a | I don't have any | 0 | 0 |
| | | b | It is a small part of my pain | 0 | 4 |
| | | c | It is a substantial part of my pain | 0 | 6 |
| | | d | It is the greatest part of my pain | 0 | 8 |
| S1Q6 | How is your pain at night? (for time> 6 months) | a | No pain | 4 | 0 |
| | | b | Much less than during the day | 3 | 1 |
| | | c | Less than during the day | 2 | 3 |
| | | d | Just as bad as during the day | 1 | 4 |
| | How is your pain at night? (for time 1 to 6 months) | a | No pain | 4 | 0 |

FIG. 2A

| | | | | |
|---|---|---|---|---|
| | b | Much less than during the day | 2 | 1 |
| | c | Less than during the day | 3 | 2 |
| | d | Just as bad as during the day | 1 | 4 |
| How is your pain at night? (for time< 1 month) | a | No pain | 4 | 0 |
| | b | Much less than during the day | 2 | 1 |
| | c | Less than during the day | 0 | 0 |
| | d | Just as bad as during the day | 0 | 0 |
| S1Q7 Does your pain wake you up at night? (for time >6 months) | a | Never | 4 | 0 |
| | b | Seldom | 2 | 1 |
| | c | Often | 2 | 3 |
| | d | Always | 0 | 4 |
| Does your pain wake you up at night? (for time 1 to 6 months) | a | Never | 4 | 0 |
| | b | Seldom | 2 | 1 |
| | c | Often | 2 | 3 |
| | d | Always | 1 | 4 |
| Does your pain wake you up at night? (for time < 1 month) | a | Never | 4 | 0 |
| | b | Seldom | 2 | 1 |
| | c | Often | 0 | 0 |
| | d | Always | 0 | 0 |
| S1Q8 Are you numb in the area of worst pain? | a | Yes | 0 | 1 |
| | b | No | 0 | 0 |
| S1Q9 Do you have any of the following in the pain area? (choose all that apply) | a | Swelling | 0 | 0 |
| | b | Change in color | 0 | 1 (if time is >1 month) |
| | c | Change in temperature | 0 | 1 |
| | d | Pain even to even light touch of the pain area | 0 | 1 |
| | e | Air blowing causes pain | 0 | 1 |
| | f | The water in the shower causes pain | 0 | 1 |
| | g | Sheets in bed bother me | 0 | 1 |

FIG. 2A (Continued)

FOR PATIENTS WITH UPPER EXTREMITY PAIN

| Question Designation 204 | Question 200 | Answer Designation 212 | Answer 208 | Nociceptive Pain Category 216 | Neuropathic Pain Category 220 |
|---|---|---|---|---|---|
| S2Q1 | What effects does activity have on your arm pain? | a | No effect on the pain | 0 | 0 |
| | | b | Minimal effect on the pain | 0 | 0 |
| | | c | Makes the pain definitely worse | 0 | 1 |
| S2Q2 | If you use the arm extensively, how long does it take for the pain to come on? | a | Immediately | 1 | 0 |
| | | b | After a few minutes | 0 | 0 |
| | | c | After a few hours | 0 | 1 |
| | | d | The next day | 0 | 1 |
| S2Q3 | When you stop using the arm, how long will the pain last? | a | Minutes | 1 | 0 |
| | | b | Hours | 0 | 1 |
| | | c | Days | 0 | 4 |
| S2Q4 | Do you have increased pain when you keep the arm elevated at or above the head level? | a | Yes | 0 | 1 |
| | | b | No | 0 | 0 |
| S2Q5 | Does your arm fatigue and hurt more with repetitive activity (for example writing)? | a | Yes | 0 | 1 |
| | | b | No | 0 | 0 |
| S2Q6 | Do you have pain in the upper chest area? | a | Yes | 0 | 1 |
| | | b | No | 0 | 0 |

FIG. 2B

FIG. 2C
SECTION 3

| | | FOR PATIENTS WITH LOWER EXTREMITY PAIN | | | |
|---|---|---|---|---|---|
| Question Designation 204 | Question 200 | Answer Designation 212 | Answer 208 | Nociceptive Pain Category 216 | Neuropathic Pain Category 220 |
| S3Q1 | Do your legs ever give out on you? | a | Yes | 0 | 1 |
| | | b | No | 0 | 0 |
| S3Q2 | Is your leg swollen even when you lie flat? | a | Yes | 0 | 1 |
| | | b | No | 0 | 1 (if time>1 month) |
| S3Q3 | Do you have problems voiding? | a | Yes | 0 | 1 |
| | | b | No | 0 | 0 |
| S3Q4 | How long have you had problems voiding? | a | < 6 months | 0 | 0 |
| | | b | > 6 month | 0 | 1 |

FIG. 2D
SECTION 4

| Question Designation 204 | Question 200 | Answer Designation 212 | Answer 208 | Nociceptive Pain Category 216 | Neuropathic Pain Category 220 |
|---|---|---|---|---|---|
| \multicolumn{6}{|l|}{FOR PATIENTS WHO HAVE HAD PREVIOUS SURGERY (NON-SPINE SURGERY RELATED TO THE EXISTING PROBLEM)} |
| S4Q1 | How many surgeries have you had? (Only the ones related to your current pain problem) | a | 1 | 0 | 0 |
| | | b | 2 | 0 | 1 |
| | | c | >2 | 0 | 2 |
| S4Q2 | Did any of the surgeries help you with your current pain for more than 6 months? | a | Yes | 1 | 0 |
| | | b | Yes, Maybe | 0 | 0 |
| | | c | No | 0 | 1 |
| S4Q3 | Was your pain made permanently worse after one of the surgeries? | a | Yes | 0 | 1 |
| | | b | No | 0 | 0 |
| | | c | Hard to tell | 0 | 0 |

FIG. 2E
SECTION 5

| | FOR PATIENTS WHO HAVE HAD PREVIOUS SPINE SURGERY | | | | |
|---|---|---|---|---|---|
| Question Designation 204 | Question 200 | Answer Designation 212 | Answer 208 | Nociceptive Pain Category 216 | Neuropathic Pain Category 220 |
| S5Q1 | How many spine surgeries have you had? (related to the existing pain problem) | a | 1 | 0 | 0 |
| | | b | 2 | 0 | 1 |
| | | c | >2 | 0 | 2 |
| S5Q2 | Did any of the spine surgeries ever help you with your neck/back pain? | a | Yes, a lot | 1 | 0 |
| | | b | Yes, moderately | 0 | 0 |
| | | c | No | 0 | 1 |
| S5Q3 | Did any of the spine surgeries ever help you with your arm(s)/leg(s) pain? | a | Yes, a lot | 1 | 0 |
| | | b | Yes, moderately | 0 | 0 |
| | | c | No | 0 | 1 |
| S5Q4 | Was your arm/leg pain made permanently worse after one of the spine surgeries? | a | Yes | 0 | 1 |
| | | b | No | 0 | 0 |
| | | c | Hard to tell | 0 | 0 |

FIG. 6

PATIENT REPORT 600

Jane Doe  ◄——— Patient Identification 604

SECTION 1

| | GENERAL QUESTIONS FOR ALL PATIENTS | | | | |
|---|---|---|---|---|---|
| Question Designation 204 | Question 200 | Answer Designation 212 | Answer 208 | Nociceptive Pain Category 216 | Neuropathic Pain Category 220 |
| S1Q1 | How frequent is your pain? | a | Constant | 1 | 4 |
| S1Q2 | How long have you had the pain? | d | More than one year | 1 | 4 |
| S1Q3 | How bad is the pain? (at its worst) | a | Excruciating | 4 | 4 |
| S1Q4 | How bad is the pain? (at its least) | c | Moderate | 2 | 1 |
| S1Q5 | About burning pain, which one applies to you? | c | It is a substantial part of my pain | 0 | 6 |
| S1Q6 | How is your pain at night? (for time> 6 months) | c | Less than during the day | 2 | 3 |
| S1Q7 | Does your pain wake you up at night? (for time > 6 months) | c | Often | 2 | 3 |
| S1Q8 | Are you numb in the area of worst pain? | a | Yes | 0 | 1 |
| S1Q9 | Do you have any of the following in the pain area? (choose all that apply) | c | Change in temperature | 0 | 1 |
| | | d | Pain even to even light touch of the pain area | 0 | 1 |
| | | f | The water in the shower causes pain | 0 | 1 |

SECTION 2

| | FOR PATIENTS WITH UPPER EXTREMITY PAIN | | | | |
|---|---|---|---|---|---|
| Question Designation 204 | Question 200 | Answer Designation 212 | Answer 208 | Nociceptive Pain Category 216 | Neuropathic Pain Category 220 |
| S2Q1 | What effects does activity have on your arm pain? | c | Makes the pain definitely worse | 0 | 1 |
| S2Q2 | If you use the arm extensively, how long does it take for the pain to come on? | d | The next day | 0 | 1 |
| S2Q3 | When you stop using the arm, how long will the pain last? | b | Hours | 0 | 1 |
| S2Q4 | Do you have increased pain when you keep the arm elevated at or above the head level? | a | Yes | 0 | 1 |

| S2Q5 | Does your arm fatigue and hurt more with repetitive activity (for example writing) ? | a | Yes | 0 | 1 |
| S2Q6 | Do you have pain in the upper chest area? | a | Yes | 0 | 1 |

Raw Nociceptive Pain Score = 12      ◄— Raw Nociceptive Pain Score 304
Raw Neuropathic Pain Score = 35      ◄— Raw Neuropathic Pain Score 308

Partial Nociceptive Pain Score = 5.7      ◄— Partial Nociceptive Pain Score 316
Partial Neuropathic Pain Score = 6.9      ◄— Partial Neuropathic Pain Score 320

Final Nociceptive Pain Score = 5.7      ◄— Final Nociceptive Pain Score 328
Final Neuropathic Pain Score = 14.4      ◄— Final Neuropathic Pain Score 332

Final Ratio = 2.5      ◄— Final Ratio 340

Pain Prediction = Neuropathic Pain      ◄— Pain Prediction 608

PATIENT REPORT 900

Jane Doe ◀────── Patient Identification 604

SECTION 1

| | GENERAL QUESTIONS FOR ALL PATIENTS | | | | |
|---|---|---|---|---|---|
| Question Designation 204 | Question 200 | Answer Designation 212 | Answer 208 | Nociceptive Pain Category 216 | Neuropathic Pain Category 220 |
| S1Q1 | How frequent is your pain? | a | Constant | 1 | 4 |
| S1Q2 | How long have you had the pain? | d | More than one year | 1 | 4 |
| S1Q3 | How bad is the pain? (at its worst) | a | Excruciating | 4 | 4 |
| S1Q4 | How bad is the pain? (at its least) | c | Moderate | 2 | 1 |
| S1Q5 | About burning pain, which one applies to you? | c | It is a substantial part of my pain | 0 | 6 |
| S1Q6 | How is your pain at night? (for time> 6 months) | c | Less than during the day | 2 | 3 |
| S1Q7 | Does your pain wake you up at night? (for time > 6 months) | c | Often | 2 | 3 |
| S1Q8 | Are you numb in the area of worst pain? | a | Yes | 0 | 1 |
| S1Q9 | Do you have any of the following in the pain area? (choose all that apply) | c | Change in temperature | 0 | 1 |
| | | d | Pain even to even light touch of the pain area | 0 | 1 |
| | | f | The water in the shower causes pain | 0 | 1 |

SECTION 2

| | FOR PATIENTS WITH UPPER EXTREMITY PAIN | | | | |
|---|---|---|---|---|---|
| Question Designation 204 | Question 200 | Answer Designation 212 | Answer 208 | Nociceptive Pain Category 216 | Neuropathic Pain Category 220 |
| S2Q1 | What effects does activity have on your arm pain? | c | Makes the pain definitely worse | 0 | 1 |
| S2Q2 | If you use the arm extensively, how long does it take for the pain to come on? | d | The next day | 0 | 1 |
| S2Q3 | When you stop using the arm, how long will the pain last? | b | Hours | 0 | 1 |
| S2Q4 | Do you have increased pain when you keep the arm elevated at or above the head level? | a | Yes | 0 | 1 |

| | | | | | |
|---|---|---|---|---|---|
| S2Q5 | Does your arm fatigue and hurt more with repetitive activity (for example writing)? | a | Yes | 0 | 1 |
| S2Q6 | Do you have pain in the upper chest area? | a | Yes | 0 | 1 |

Raw Nociceptive Pain Score = 12 ← Raw Nociceptive Pain Score 304
Raw Neuropathic Pain Score = 35 ← Raw Neuropathic Pain Score 308

Partial Nociceptive Pain Score = 5.7 ← Partial Nociceptive Pain Score 316
Partial Neuropathic Pain Score = 6.9 ← Partial Neuropathic Pain Score 320

Final Nociceptive Pain Score = 5.7 ← Final Nociceptive Pain Score 328
Final Neuropathic Pain Score = 14.4 ← Final Neuropathic Pain Score 332

Final Ratio = 2.5 ← Final Ratio 340

Pain Prediction = Neuropathic Pain ← Pain Prediction 608

Comparison Data 904
Top 3 Matches

1 Percent (%) Answer Match With Patient #1 = 94%
   Patient #1 Final Ratio = 2.4
   Patient #1 Treatment = Neurostimulation
   Patient #1 Description of Treatment Effectiveness = Good

2 Percent (%) Answer Match With Patient #2 = 85%
   Patient #2 Final Ratio = 2.8
   Patient #2 Treatment = Neurostimulation
   Patient #2 Description of Treatment Effectiveness = Excellent

3 Percent (%) Answer Match With Patient #3 = 79%
   Patient #3 Final Ratio = 2.2
   Patient #3 Treatment = Neurostimulation
   Patient #3 Description of Treatment Effectiveness = Good

Fig. 9 Continued

METHOD AND SYSTEM FOR DISTINGUISHING NOCICEPTIVE PAIN FROM NEUROPATHIC PAIN

CROSS REFERENCE TO RELATED APPLICATIONS

This application is a continuation of U.S. Ser. No. 12/102,322 filed on Apr. 14, 2008, which claims the benefit of U.S. Provisional Application No. 60/915,295 filed on May 1, 2007, incorporated by reference herein. The present application claims the benefit of each of the foregoing applications.

FIELD

The present invention is related to diagnosing pain in a patient, and more particularly, the present invention is related to a method of distinguishing whether a patient's pain is nociceptive pain, neuropathic pain, or both nociceptive pain and neuropathic pain.

BACKGROUND

The following text should not be construed as an admission of knowledge in the prior art. Furthermore, citation or identification of any document in this application is not an admission that such document is available as prior art to the present invention, or that any reference forms a part of the common general knowledge in the art.

Pain can be caused by a variety of diseases and injuries. A significant difficulty in the treatment of pain is properly diagnosing the cause of the pain. That is, once a physician has identified the nature of the pain, treating the pain or the cause of the pain can be more successful than attempting to treat the pain or the cause of the pain if the physician cannot accurately identify the nature of the patient's pain. Thus, if the treating physician cannot first correctly identify the nature of the patient's pain, the physician may try to treat the pain in a manner that will not bring relief to the patient because the pain has a different source than the false source identified by the physician. For example, if a patient is experiencing pain in his or her shoulder, the pain could be caused by scar tissue from a prior surgery performed in the proximity of the patient's rotator cuff. Here, the mechanical action of the patient's rotator is impaired by the scar tissue, thereby causing inflammation in the vicinity of the rotator cuff and associated pain. To treat the patient's pain, the physician may adequately address the pain by a surgical procedure to remove the scar tissue. On the other hand, if the patient's pain is caused by nerve damage, removing or attempting to remove scar tissue will not necessarily bring the patient any relief from the pain. Indeed, the patient may ultimately experience more pain because of undergoing the surgical procedure, which could possibly lead to other complications. In contrast, if the treating physician were to have properly identified that the cause of the patient's pain was a neurological source, then such recurring pain may have been properly addressed using another treatment, such as neurostimulation.

It is generally accepted that there are two main types of pain. One type of pain is called nociceptive pain, and this type of pain is the normal physiological pain that is associated with a warning signal that something is threatening the person's bodily tissues. Therefore, nociceptive pain serves to alert or signal a person that appropriate measures can possibly be taken to avoid or mitigate further tissue damage. Nociceptive pain is transmitted through the spino-thalamic tract and is the type of pain that people normally experience from a disease or injury. Thus, by way of example, nociceptive pain occurs after mechanical, chemical, and/or thermal stimulation of A-delta and C-polymodal pain receptors. Examples of nociceptive pain are sprains and/or strains, broken bones, lower back pain from disc disease or injury, and burns.

In contrast, neuropathic pain is pain that is caused by damage to the person's nervous system. Neuropathic pain is pain that a person experiences due to transmission of pain signals in the absence of actual tissue damage. However, neuropathic pain can also be a sequela of nociceptive pain if damage to the nervous tissue also occurred with an injury. Thus, with neuropathic pain, the nerve fibers themselves may be damaged or injured and send signals that are interpreted by the person's brain as pain. Neuropathic pain often becomes chronic and lasts over 6 months, and can also become a permanent condition. When this occurs, the neuropathic pain serves no real protective biological function, because it is not serving to warn the person of an injury to allow the person to act to avoid further harm. Rather, the neuropathic pain is the problem itself. Thus, rather than being the symptom of a disease or a warning of injury, the chronic neuropathic pain is itself the disease. With neuropathic pain, the pain the person is experiencing is real, but it is not useful because the person cannot take action to remedy or mitigate a disease or injury. Examples of neuropathic pain include instances when a patient experiences sensations described as hot, cold, shocking, burning, electrical or numbness, and where the pain is attributable to a non-injury source, such as shingles, thalamic stroke, and diabetic neuropathy.

The treatment for nociceptive pain is to remove the offending cause. The pain will automatically disappear. Thus, nociceptive pain can be cured. In contrast, neuropathic pain cannot be cured. The goal of the treatment for neuropathic pain is to try to decrease the pain. Often times a patient will have a mixed condition, where both types of pain coexist in different percentages.

It is, therefore, important to try to distinguish nociceptive pain from neuropathic pain so that the appropriate treatment can be formulated. More surgical interventions on someone with neuropathic pain will inevitably lead to failure and further pain. Unfortunately, often the situation is not so clear, and it might be difficult to separate the two types of pain. Complicating this issue is that nociceptive pain and neuropathic pain can often coexist. Sometimes the nociceptive component is dominant, other times the neuropathic component is the prevalent one.

Descriptors exist in the literature that characterize the two types of pain. However, unless a physician is truly experienced in the pain field, a true differentiation might be difficult. Often times the physician does not ask the proper questions or does not correctly assess the answers. Pain scales currently available assess the severity of the pain, the verbal descriptors of the pain, and the impact of the pain on the psychological and social milieu of the patient.

One such method is known as the Visual Analogue Rating scale ("VAS"). See Huskisson, "Measurement of Pain," *Lancet*, 1974; 2:1127-1131, the content of which is incorporated herein by reference. VAS may be the most widespread pain intensity measurement scale. However, VAS does not differentiate between types of symptoms, but purely assigns a numerical value to the intensity of the pain.

A second method of describing pain is the McGill Pain Questionnaire ("MPQ"). See Melzack, "The McGill Pain Questionnaire: Major Properties and Scoring Methods," *Pain*, 1975, 1:277-299, the content of which is incorporated herein by reference. The MPQ incorporates a series of adjectives to describe the characteristics and intensity of a patient's pain. In addition, the MPQ uses a mannequin to allow the patient draw the areas of pain. The MPQ is used to specify subjective pain experience using sensory, affective and evaluative word descriptors. There are three major measures: the pain rating index, based on two types of numerical values that can be assigned to each word descriptor; the number of words chosen; and the present pain intensity based on a 1-5 intensity scale. The MPQ was developed to indicate the extent of change in pain quality and intensity as a result of an intervention.

Yet another method of describing pain is the Wisconsin Brief Pain Questionnaire ("BPQ"). BPQ is described as a self-administered instrument that assesses pain. The BPQ uses a human figure that is shaded to indicate pain, rating of pain intensity, relief from medication, and ratings of pain interference. A 0-4 scale is used. The BPQ was used as an outcome measure in a study of pain in ambulatory HIV patients. See McCormack et al., "Inadequate Treatment of Pain in Ambulatory HIV Patients," *Clin. J. Pain,* 1993, 9:279-83. The study was able to show that pain control in this population is inadequate with usual intervention. The BPQ has been used in cancer, rheumatoid arthritis and HIV patients. See Daut et al., "Development of the Wisconsin Brief Pain Questionnaire to Assess Pain in Cancer and Other Diseases, *Pain,* 1983, 17:197-210, the content of which is incorporated herein by reference.

The Battery for Health Improvement 2 ("BHI 2") is described as an assessment of the biopsychosocial issues that are relevant in evaluating medical patients. The BHI 2 test is described as being able to help caregivers shape an appropriate treatment plan, reduce treatment time and improve a patient's quality of life.

Still another method of describing pain is the Minnesota Multiphasic Personality Inventory-2 ("MMPI-2"). The MMPI-2 is a test of adult psychopathology and is used by clinicians to assist with the diagnosis of mental disorders and the selection of appropriate treatment methods. The MMPI-2 test is described as being able to help assess medical patients and design effective treatment strategies, including chronic pain management. However, MMPI-2 does not have any questions related to nociceptive pain symptoms and does not allow a differentiation between the two types of pain.

Yet another method of describing pain is the Neuropathic Pain Scale ("NPS"). The NPS is described as being able to measure the intensity of different symptoms that are associated with neuropathic pain. However, NPS does not have any questions related to nociceptive pain symptoms and does not allow a differentiation between the two types of pain.

Although some prescribed drugs can be helpful for addressing neuropathic pain, certain individuals can have difficulties with various side effects associated with pain relieving drugs. Neurostimulation is a method that can be used for treating chronic neuropathic pain. Accordingly, in some instances, electrical stimulation of nerves within the body can be used to control pain of a patient suffering from chronic neuropathic pain. However, to properly treat the neuropathic pain, the physician must first be able to diagnose that the pain originates from a neurological source, and herein lies the problem because the cause of a person's pain is not necessarily easy to discover.

Accordingly, it would be beneficial to have a method of properly identifying the nature of the patient's pain so that the treating physician can undertake steps to properly treat the patient, thereby providing the patient relief. In addition, it would be advantageous to provide a system for assisting a physician to identify whether a patient's pain is nociceptive pain or neuropathic pain, and it would be help to also provide a process for assisting a physician to distinguish nociceptive pain from neuropathic pain using information provided by a patient.

Nothing herein is to be construed as an admission that the present invention is not entitled to antedate a publication by virtue of prior invention. Furthermore, the dates of publication where provided are subject to change if it is found that the actual date of publication is different from that provided here.

SUMMARY

The present invention is directed to a weighted scoring system based on a questionnaire filled in by the patient and/or the physician. The questions are designed to provide information to allow the differentiation of nociceptive pain from neuropathic pain. Thus, the questionnaire includes questions that are meant to differentiate the two types of pain. The questions are divided in five sections or parts: a first section or part of the questionnaire is common for all areas of pain; and subsets of questions that are directed to specific cases of upper extremity pain, lower extremity pain, patients who underwent previous surgery for the condition, and patients who underwent previous spine surgery for the condition.

In general, each question has multiple answers, and each answer has a different weighted score. The patient fills out the questionnaire in the appropriate sections. The score from the first or common section is enough by itself to establish a weighted differential between the two types pain; however, the other four sections of questions help further define the differential and strengthen the score. A different score is kept for the nociceptive pain component and the neuropathic pain component. Thus, for each of the answers to the questions there are two separate scores, one for nociceptive pain and one for neuropathic pain. The scores are added together within each type of pain to provide a raw nociceptive pain score and a raw neuropathic pain score. These raw scores are then multiplied by a multiplier or coefficient. There are different scenarios with different multipliers or coefficients. In addition, if certain questions were given certain answers, additional scores are added to resultants and then a final ratio is computed.

In addition, embodiments of the present invention include a system for assisting a physician to identify whether a patient's pain is nociceptive pain or neuropathic pain. Embodiments of the present invention are also directed to a process for assisting a physician to distinguish nociceptive pain from neuropathic pain using information provided by a patient. More particularly, in accordance with at least one embodiment of the present invention, a system is provided wherein a physician utilizes a computational device that includes a series of questions for presentation to the patient, medical staff member, and/or physician. The computation device can automatically calculate the various computational components used in the method described above and can provide the physician with diagnosis information. In accordance with at least one embodiment of the present invention, a laptop computer or handheld device is used for presenting the patient, medical care assistant, and/or physician with a series of questions for diagnosing the patient's pain. By way of example and not limitation, the computation device may comprise a wireless handheld computer that allows presentation of the questions, and further enables the collection, sending, and receiving of data electronically. With the information provided by the system, the physician can then evaluate the one or more components of the two types of pain, and then formulate a more focused treatment plan accordingly.

In addition, in accordance with at least one embodiment of the present invention, a database calculation and/or comparison system and/or service is provided, wherein a physician can upload a patient's information from a questionnaire and results are calculated and/or a comparison is performed to provide the physician with diagnosis information. In accordance with embodiments of the present invention, a physician first provides a patient with the questionnaire and/or goes through the questions with the patient to generate answers for a plurality of questions that provide the physician with information concerning the nature of the patient's pain and surrounding symptoms. Such questions are described above and are not repeated here. Once the physician has answers to the questions, the physician may then upload the answers to a server associated with the service. Alternatively, a calculation and comparison program may be provided on compact disc to the physician. In at least one embodiment, a report is provided to the physician with diagnosis, listing of treatment options, and probability of treatment success.

It is to be understood that the present invention includes a variety of different versions or embodiments, and this Summary is not meant to be limiting or all-inclusive. This Summary provides some general descriptions of some of the embodiments, but may also include some more specific descriptions of certain embodiments.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The terms "determine", "calculate" and "compute," and variations thereof, as used herein, are used interchangeably and include any type of methodology, process, mathematical operation or technique.

The term "automatic" and variations thereof, as used herein, refers to any process or operation done without material human input when the process or operation is performed. However, a process or operation can be automatic even if performance of the process or operation uses human input, whether material or immaterial, received before performance of the process or operation. Human input is deemed to be material if such input influences how the process or operation will be performed. Human input that consents to the performance of the process or operation is not deemed to be "material".

The term "module" as used herein refers to any known or later developed hardware, software, firmware, artificial intelligence, fuzzy logic, or combination of hardware and software that is capable of performing the functionality associated with that element. Also, while the invention is described in terms of exemplary embodiments, it should be appreciated that individual aspects of the invention can be separately claimed.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIGS. 1A and 1B are a flow chart illustrating the various steps of a method in accordance with an embodiment of the present invention;

FIGS. 2A-2E are series of questions for use in accordance with at least one embodiment of the present invention;

FIG. 6 is an exemplary patient report in accordance with embodiments of the present invention;

FIG. 9 is another exemplary patient report in accordance with embodiments of the present invention.

The drawings are not necessarily to scale.

DETAILED DESCRIPTION

In accordance with at least one embodiment of the invention, a method of distinguishing nociceptive pain from neuropathic pain is provided. The method includes providing a series of questions for answering by the patient and/or the physician or a medical staff member. In one embodiment, each of the answers by the patient is given a numerical value in both a nociceptive pain category and a neuropathic pain category. The values within the two categories are then summed, with the resultants further modified using a series of one or more equations. The modified resultant provides a ratio or rating value for the physician to diagnose the patient as suffering from nociceptive pain, neuropathic pain, or both nociceptive pain and neuropathic pain.

Figure 1A:
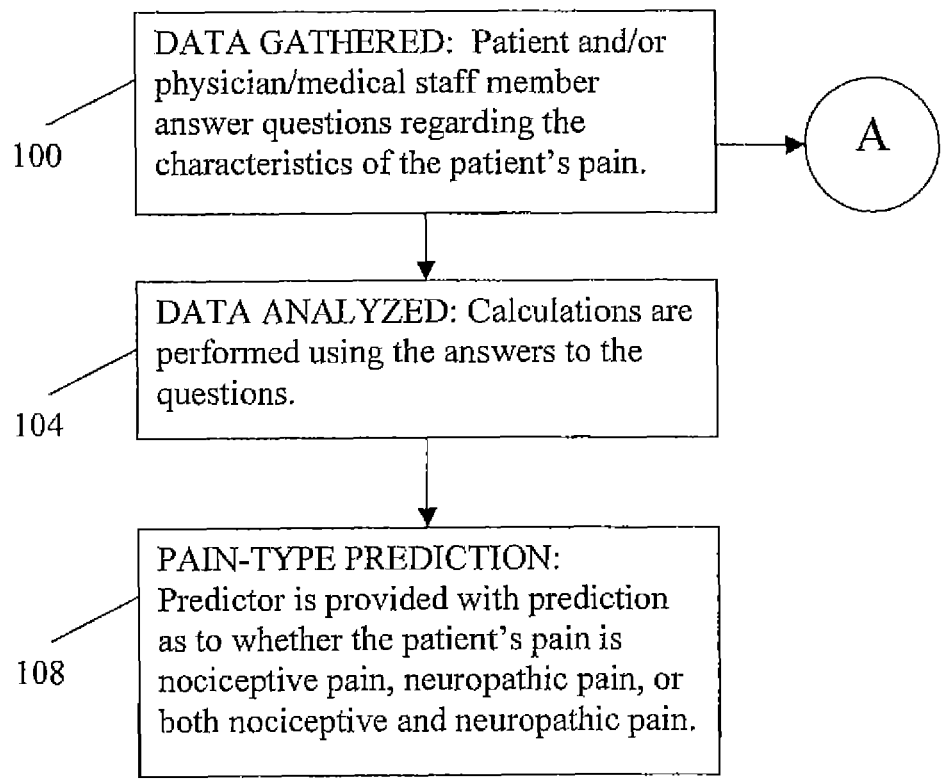

Referring now to FIG. 1A, a flowchart is shown that depicts the steps involved in a first embodiment of the invention. In step 100, data is gathered by having the patient and/or the physician or a medical staff member answer questions about the patient's pain. As discussed in further detail below, step 100 may further comprise using a computer device to present the questions and/or record the answers. However, as those skilled in the art will appreciate, the data does not have to be entered into a computer device. That is, the patient could be asked to answer questions appearing on one or more sheets of paper.

In step 104, the data gathered in step 100 is analyzed. That is, in step 104 data analysis occurs that includes performing calculations using the answers to the questions answered in step 100. In step 108, a final ratio, final resultant or predictor is provided to the physician, wherein the prediction is directed to whether the patient's pain is nociceptive pain, neuropathic pain, or both nociceptive and neuropathic pain. Each of the above noted steps are now described in detail and/or further expanded upon.

As noted above, the method includes step 100 comprising gathering data, and in at least one embodiment, step 100 includes having the patient answer a series of questions that seek specific information concerning the patient's pain. In accordance with embodiments of the present invention, FIGS. 2A-2E provide an example listing of questions for obtaining information from the patient to assist the physician in determining whether the patient is suffering from nociceptive pain, neuropathic pain, or both nociceptive pain and neuropathic pain. As those skilled in the art will appreciate, the questions may be modified from those described or listed herein, because the purpose of the questions is to gain information that properly and correctly characterizes the nature of the patient's pain. Therefore, modifications, revisions and/or different questions may be appropriate, particularly as advances in medicine aid physicians in finding ways to characterize the patient's pain. Notwithstanding possible future revisions to the questions given in FIG. 2A-2E, when used with the current method described herein, the questions provide a way of distinguishing nociceptive pain from neuropathic pain. It is noted that the questions and point values associated with the answers are designed to mathematically operate in conjunction with the multipliers and equations set out below. Thus, if modifications are made to the questions and the point values associated with their answers, modifications may also be required of the multipliers and equations. Such modifications to the questions, answer point values, multipliers and equations are considered to lie within the scope of the present invention.

Referring now to FIG. 2A through 2E, the questions 200 are divided into Sections 1 through 5, respectively. Section 1 includes questions for all patients. Sections 2-5 include optional additional questions depending upon whether the patient meets prerequisite conditions for the use of the questions 200 in one or more of Sections 2-5.

For ease of reference herein, the questions 200 include question designations 204, wherein the question designations 204 are structured as "S1Q1" for Section 1, Question 1; "S1Q2" for Section 1, Question 2, and so on. Within Section 1 of the questions 200 shown in FIG. 2A, general questions concerning the pain are provided, such as S1Q1 "How frequent is your pain?" and S1Q2 "How long have you had the pain?" Here, the patient responds to the questions 200 by choosing a proper answer 208 to describe their pain. Answers may have an answer designation 212, such as "(a)", "(b)", "(c)", or "(d)". For example, in response to the question designation S1Q1 "How frequent is your pain?" the patient may respond by answering (a) "Constant," (b) "Not constant: every day frequently," (c) "Not constant: every day infrequently," or (d) "Not constant: not every day."

For each answer designation 212, the method utilizes a pair of point systems within two categories. The first category is the nociceptive pain category 216, and the second category is the neuropathic pain category 220. Although the values in each category 216 and 220 for a given answer designation 212 may be the same, the values generally reflect the tendency for the answer's importance with regard to the specific category. So, for example, if the question 200 is question designation S1Q2 "How long have you had the pain?" the patient may respond with one of four answers, where answer (a) "Less than a month" is assigned a point value of "1" in the nociceptive pain category 216 and this same answer is assigned a point value of "0" in the neuropathic pain category 220. Considering an alternate answer to question designation S1Q2, if the patient answers (d) "More than one year," here, this response is assigned a point value of "1" in the nociceptive pain category 216 and this same answer is assigned a point value of "4" in the neuropathic pain category 220. Thus, the point values assigned in each category 216 and 220 increase with the tendency for the patient's answer to be an important indicator of whether the patient's pain is nociceptive pain or neuropathic pain. Thus, for the last example given of question designation S1Q2, since neuropathic pain tends to be a long-term ongoing type of pain, a point value of "4" was given within the neuropathic pain category 220 for answer designation (d) "More than one year," because long-term ongoing pain it is a strong indicator of neuropathic pain. It is noted that modifications to the method could entail using an inverse type of point value system wherein lower point values are used to indicate a tendency toward indicating a type of pain, and for such modifications, the multipliers and equations could be adjusted to accommodate such an alternative valuation system. Again, such modifications to the point values, multipliers and equations are considered variations of the present embodiment and are within the scope of the invention.

Referring now to FIG. 2B, questions 200 for Section 2 are presented. Here, Section 2 questions are answered if the patient suffers from upper extremity pain. If the patient does not suffer from upper extremity pain, then the questions 200 in Section 2 are skipped.

Referring now to FIG. 2C, questions 200 for Section 3 are presented. Here, Section 3 questions are answered if the patient suffers from lower extremity pain. If the patient does not suffer from lower extremity pain, then the questions 200 in Section 3 are skipped.

Referring now to FIG. 2D, questions 200 for Section 4 are presented. Here, Section 4 questions are answered if the patient has had previous surgery other than spine surgery because of the pain. Again, if the patient has not had previous surgery other than spine surgery because of the pain, then the questions 200 in Section 4 are skipped.

Referring now to FIG. 2E, questions 200 for Section 5 are presented. Here, Section 5 questions are answered if the patient has had previous spine surgery because of the pain. Again, if the patient has not had previous spine surgery because of the pain, then the questions 200 in Section 5 are skipped.

Referring again to FIG. 1A, after the data is gathered at step 100, the data is analyzed at step 104. Here, calculations are performed using the numerical values noted above that were assigned to the answers 208 for the questions 200, where the numerical values are given in both the nociceptive pain category 216 and the neuropathic pain category 220.

Figure 3:
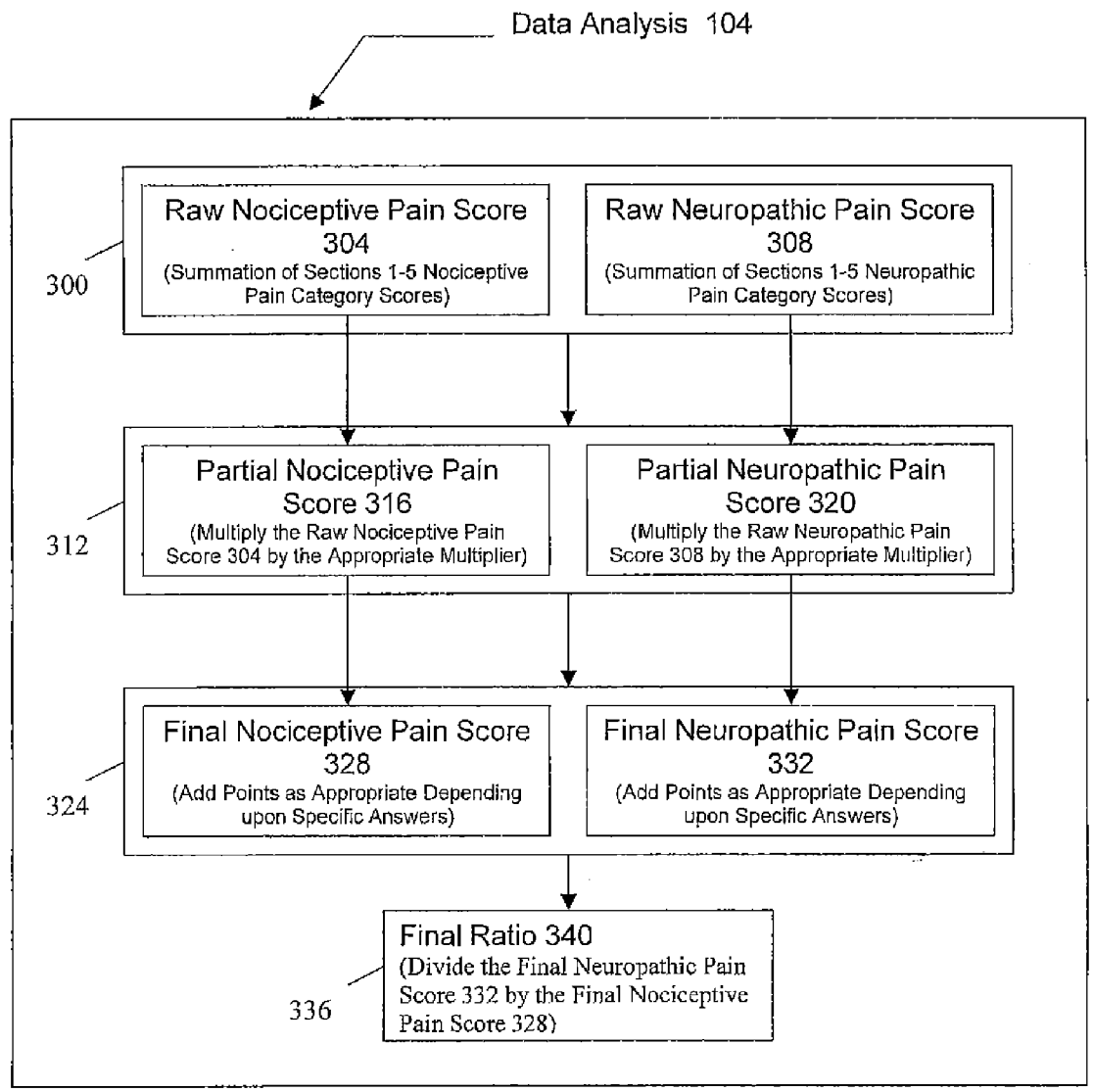
FIG. 3 is a flowchart of the data analysis step of a method in accordance with an embodiment of the present invention.

The following discussion presents the steps of the analysis shown in FIG. 3. FIG. 3 illustrates the substeps to analyzing the data in step 104 using the information gathered in step 100. In substep 300 the point values from Sections 1 through 5 are added. More specifically, in substep 300 the raw nociceptive pain score 304 is calculated by summing the answer values in the nociceptive pain category 216. Likewise, in substep 300 the raw neuropathic pain score 308 is also calculated by summing the answer values in the neuropathic pain category 220. Thus, data analysis of substep 300 yields two resultants, the first resultant is the raw nociceptive pain score (RnocPS) 304, and the second resultant is the raw neuropathic pain score (RneuPS) 308. That is, $$\text{RnocPS} = \Sigma \text{ Points in nociceptive pain category } 216 \quad \text{Equation 1}$$

$$\text{RneuPS} = \Sigma \text{ Points in neuropathic pain category } 220 \quad \text{Equation 2}$$

Still referring to FIG. 3, in step 312 the partial nociceptive pain score (PnocPS) 316 and the partial neuropathic pain score (PneuPS) 320 are calculated by multiplying the raw nociceptive pain score 304 of Equation 1 and the raw neuropathic pain score 308 of Equation 2, respectively, by the appropriate multiplier. That is, $$PnocPS = \text{First Multiplier} \times (RnocPS); \text{ and}$$

$$PneuPS = \text{Second Multiplier} \times (RneuPS).$$

The appropriate multipliers are listed in the table of calculation multipliers provided as Table 1, and the actual multiplier used depends upon whether the patient has upper or lower extremity pain and/or whether the patient has undergone any surgery.

TABLE 1

MULTIPLIERS

| | | Multiplier Designation |
|---|---|---|
| General Pain | | A |
| Nociceptive | 0.526 | |
| Neuropathic | 0.2439 | |
| Upper extremity | | B |
| Nociceptive | 0.4761 | |
| Neuropathic | 0.196 | |
| Lower Extremity | | C |
| Nociceptive | 0.5263 | |
| Neuropathic | 0.2272 | |
| General Pain + Surgery | | D |
| Nociceptive | 0.5 | |
| Neuropathic | 0.2127 | |
| Upper Extremity + Surgery | | E |
| Nociceptive | 0.4545 | |
| Neuropathic | 0.1851 | |
| Lower Extremity + Surgery | | F |
| Nociceptive | 0.5 | |
| Neuropathic | 0.2083 | |
| General Pain + Spine Surgery | | G |
| Nociceptive | 0.476 | |
| Neuropathic | 0.2173 | |
| Upper Extremity + Spine Surgery | | H |
| Nociceptive | 0.4347 | |
| Neuropathic | 0.1818 | |
| Lower Extremity + Spine Surgery | | I |
| Nociceptive | 0.4761 | |
| Neuropathic | 0.204 | |

The following text describes how the appropriate multiplier is chosen for a given case.

Referring now to Table 1, the multiplier for the circumstances where the patient has only responded to questions 200 in Section 1 for describing their general pain, multiplier designation A is to be used. Thus, for general pain alone the equations for calculating the partial nociceptive pain score (PnocPS) 316 and the partial neuropathic pain score (PneuPS) 320 are Equations 3 and 4 as follows:

$$PnocPS = 0.526 \times (RnocPS) \qquad \text{Equation 3}$$

$$PneuPS = 0.2349 \times (RneuPS) \qquad \text{Equation 4}$$

Referring again to Table 1, the multiplier for the circumstances where the patient has responded to questions 200 in Section 1 and also in Section 2 for upper extremity pain, multiplier designation B is to be used. Thus, for upper extremity pain the equations for calculating the partial nociceptive pain score (PnocPS) 316 and the partial neuropathic pain score (PneuPS) 320 are Equations 5 and 6 as follows:

$$PnocPS = 0.4761 \times (RnocPS) \qquad \text{Equation 5}$$

$$PneuPS = 0.196 \times (RneuPS) \qquad \text{Equation 6}$$

Referring yet again to Table 1, the multiplier for the circumstances where the patient has responded to questions 200 in Section 1 and also in Section 3 for lower extremity pain, multiplier designation C is to be used. Thus, for lower extremity pain the equations for calculating the partial nociceptive pain score (PnocPS) 316 and the partial neuropathic pain score (PneuPS) 320 are Equations 7 and 8 as follows:

$$PnocPS = 0.5263 \times (RnocPS) \qquad \text{Equation 7}$$

$$PneuPS = 0.2272 \times (RneuPS) \qquad \text{Equation 8}$$

Referring still yet again to Table 1, the multiplier for the circumstances where the patient has responded to questions 200 in Section 1 and also in Section 4 for surgery, multiplier designation D is to be used. Thus, for surgery the equations for calculating the partial nociceptive pain score (PnocPS) 316 and the partial neuropathic pain score (PneuPS) 320 are Equations 9 and 10 as follows:

$$PnocPS = 0.5 \times (RnocPS) \qquad \text{Equation 9}$$

$$PneuPS = 0.2127 \times (RneuPS). \qquad \text{Equation 10}$$

Referring still to Table 1, the multiplier for the circumstances where the patient has responded to questions 200 in Section 1 and also in Sections 2 and 4 for upper extremity pain and surgery, multiplier designation E is to be used. Thus, for upper extremity pain and surgery the equations for calculating the partial nociceptive pain score (PnocPS) 316 and the partial neuropathic pain score (PneuPS) 320 are Equations 11 and 12 as follows:

$$PnocPS = 0.4545 \times (RnocPS) \qquad \text{Equation 11}$$

$$PneuPS = 0.1851 \times (RneuPS) \qquad \text{Equation 12}$$

Referring still to Table 1, the multiplier for the circumstances where the patient has responded to questions 200 in Section 1 and also in Sections 3 and 4 for lower extremity pain and surgery, multiplier designation F is to be used. Thus, for lower extremity pain and surgery the equations for calculating the partial nociceptive pain score (PnocPS) 316 and the partial neuropathic pain score (PneuPS) 320 are Equations 13 and 14 as follows:

$$PnocPS = 0.5 \times (RnocPS) \qquad \text{Equation 13}$$

$$PneuPS = 0.2083 \times (RneuPS) \qquad \text{Equation 14}$$

Referring still yet again to Table 1, the multiplier for the circumstances where the patient has responded to questions 200 in Section 1 and also in Section 5 for spine surgery, multiplier designation G is to be used. Thus, for spine surgery the equations for calculating the partial nociceptive pain score (PnocPS) 316 and the partial neuropathic pain score (PneuPS) 320 are Equations 15 and 16 as follows:

$$PnocPS = 0.476 \times (RnocPS) \quad \text{Equation 15}$$

$$PneuPS = 0.2173 \times (RneuPS) \quad \text{Equation 16}$$

Referring still to Table 1, the multiplier for the circumstances where the patient has responded to questions 200 in Section 1 and also in Sections 2 and 5 for upper extremity pain and spine surgery, multiplier designation H is to be used. Thus, for upper extremity pain and spine surgery the equations for calculating the partial nociceptive pain score (PnocPS) 316 and the partial neuropathic pain score (PneuPS) 320 are Equations 17 and 18 as follows:

$$PnocPS = 0.4347 \times (RnocPS) \quad \text{Equation 17}$$

$$PneuPS = 0.1818 \times (RneuPS) \quad \text{Equation 18}$$

Referring still to Table 1, the multiplier for the circumstances where the patient has responded to questions 200 in Section 1 and also in Sections 3 and 5 for lower extremity pain and spine surgery, multiplier designation I is to be used. Thus, for lower extremity pain and spine surgery the equations for calculating the partial nociceptive pain score (PnocPS) 316 and the partial neuropathic pain score (PneuPS) 320 are Equations 19 and 20 as follows:

$$PnocPS = 0.4761 \times (RnocPS) \quad \text{Equation 19}$$

$$PneuPS = 0.204 \times (RneuPS) \quad \text{Equation 20}$$

For all cases given above, the raw nociceptive pain score (RnocPS) 304 and the raw neuropathic pain score (RneuPS) 308 are taken from the summation of the point values corresponding to the answers chosen to questions 200 in Sections 1-5. However, the partial nociceptive pain score (PnocPS) 316 and the partial neuropathic pain score (PneuPS) 320 are calculated based on multipliers chosen from Table 1, where the choice of the multiplier depends upon whether and which of the one or more of questions within Sections 2 through 5 are answered in addition to Section 1.

Referring again to FIG. 3, after calculating the partial nociceptive pain score (PnocPS) 316 and the partial neuropathic pain score (PneuPS) 320, the next substep 324 of the data analysis 104 is to calculate the final nociceptive pain score (FnocPS) 328 and the final neuropathic pain score (FneuPS) 332. The final nociceptive pain score (FnocPS) 328 and the final neuropathic pain score (FneuPS) 332 are calculated by adding point values or adjustment points (AP) for specific instances of the patient providing answers designations 212 to certain questions 200 of Sections 1 and 2 as shown in FIGS. 2A and 2B, respectively. Therefore, if the patient provided answers meeting the requirements of certain conditions, then the partial nociceptive pain score (PnocPS) 316 and the partial neuropathic pain score (PneuPS) 320 are modified in substep 324 by adding adjustment points (AP) to arrive at the final nociceptive pain score (FnocPS) 328 and the final neuropathic pain score (FneuPS) 332. However, if the patient did not provide answers meeting the requirements of the conditions, then the partial nociceptive pain score (PnocPS) 316 and the partial neuropathic pain score (PneuPS) 320 are not modified in step 324, and the partial nociceptive pain score (PnocPS) 316 and the partial neuropathic pain score (PneuPS) 320 become the final nociceptive pain score (FnocPS) 328 and the final neuropathic pain score (FneuPS) 332, respectively.

The following listing sets forth the nine conditions for modifying the partial nociceptive pain score (PnocPS) 316 and the partial neuropathic pain score (PneuPS) 320 in substep 324 to arrive at the final nociceptive pain score (FnocPS) 328 and the final neuropathic pain score (FneuPS) 332:

Condition #1: If S1Q1=a and S1Q2=a, add 3 points to the partial nociceptive pain score (PnocPS) 316.

Condition #2: If S1Q1=a and S1Q2=b, add 1 point to the partial nociceptive pain score (PnocPS) 316.

Condition #3: If S1Q2=b, c, or d and S1Q5=d, add 2 points to the partial neuropathic pain score (PneuPS) 320.

Condition #4: If S1Q2=b, c, or d and S1Q5=c, add 1.5 points to the partial neuropathic pain score (PneuPS) 320.

Condition #5: If S1Q2=b, c, or d and S1Q5=b, add 1 point to the partial neuropathic pain score (PneuPS) 320.

Condition #6: If S1Q6=d and S1Q7=cord and S1Q2=cord add 1.5 points to the partial neuropathic pain score (PneuPS) 320.

Condition #7: If S1Q9 has two or more answers of a through g, add 5 points to the partial neuropathic pain score (PneuPS) 320.

Condition #8: If S2Q3=c, add 2 points to the partial neuropathic pain score (PneuPS) 320.

Condition #9: If S2Q3=b, add 1 point to the partial neuropathic pain score (PneuPS) 320.

Thus, the answers designations 212 to certain questions 200 are checked, and if answered in accordance with one or more of Conditions #1-9 set out above, then the partial nociceptive pain score 316 and/or the partial neuropathic pain score 320 are adjusted. That is, $$FnocPS = PnocPS + AP \quad \text{Equation 21}$$

$$FneuPS = PneuPS + AP \quad \text{Equation 22}$$

Referring again to FIG. 3, after calculating the final nociceptive pain score (FnocPS) 328 and the final neuropathic pain score (FneuPS) 332, the next substep 336 of the data analysis 104 is to calculate the final ratio 340 at step 336. More particularly, the final ratio 340 is obtained by dividing the final neuropathic pain score (FneuPS) 332 by the final nociceptive pain score (FnocPS) 328. That is, $$\text{Final Ratio} = \frac{FneuPS}{FnocPS} \text{ or} \quad \text{Equation 23}$$

The final ratio 340 calculated at step 336 is the value used to assess whether the patient is suffering from nociceptive pain, neuropathic pain, or both nociceptive and neuropathic pain. If the final ratio 340 is below 1, there is a strong possibility that the pain is nociceptive. If the final ratio 340 is between 1 and 2, there is a strong possibility that the patient is suffering from a combination of both nociceptive pain and neuropathic pain. If the final ratio 340 is above 2, there is a strong possibility that the pain is neuropathic. A final ratio 340 above 4 is absolutely indicative of neuropathic pain.

The following examples are provided to assist in understanding the steps of the method of the present invention.

EXAMPLE #1

In accordance with FIG. 1A, the first 100 is to gather information per the questions listed in Sections 1-5 of FIGS. 2A-2E. For these questions, the patient answered questions 200 in Sections 1 and 2 as follows:

Section 1

GENERAL QUESTIONS FOR ALL PATIENTS

| Question Designation 204 | Question 200 | Answer Designation 212 | Answer 208 | Nociceptive Pain Category 216 | Neuropathic Pain Category 220 |
|---|---|---|---|---|---|
| S1Q1 | How frequent is your pain? | a | Constant | 1 | 4 |
| S1Q2 | How long have you had the pain? | d | More than one year | 1 | 4 |
| S1Q3 | How bad is the pain? (at its worst) | a | Excruciating | 4 | 4 |
| S1Q4 | How bad is the pain? (at its least) | c | Moderate | 2 | 1 |
| S1Q5 | About burning pain, which one applies to you? | c | It is a substantial part of my pain | 0 | 6 |
| S1Q6 | How is your pain at night? (for time >6 months) | c | Less than during the day | 2 | 3 |
| S1Q7 | Does your pain wake you up at night? (for time >6 months) | c | Often | 2 | 3 |
| S1Q8 | Are you numb in the area of worst pain? | a | Yes | 0 | 1 |
| S1Q9 | Do you have any of the following in the pain area? (choose all that apply) | c | Change in temperature | 0 | 1 |
|  |  | d | Pain even to even light touch of the pain area | 0 | 1 |
|  |  | f | The water in the shower causes pain | 0 | 1 |

Section 2

| Question Designation 204 | Question 200 | Answer Designation 212 | Answer 208 | Nociceptive Pain Category 216 | Neuropathic Pain Category 220 |
|---|---|---|---|---|---|
| | FOR PATIENTS WITH UPPER EXTREMITY PAIN | | | | |
| S2Q1 | What effects does activity have on your arm pain? | c | Makes the pain definitely worse | 0 | 1 |
| S2Q2 | If you use the arm extensively, how long does it take for the pain to come on? | d | The next day | 0 | 1 |
| S2Q3 | When you stop using the arm, how long will the pain last? | b | Hours | 0 | 1 |
| S2Q4 | Do you have increased pain when you keep the arm elevated at or above the head level? | a | Yes | 0 | 1 |
| S2Q5 | Does your arm fatigue and hurt more with repetitive activity (for example writing)? | a | Yes | 0 | 1 |
| S2Q6 | Do you have pain in the upper chest area? | a | Yes | 0 | 1 |

As seen above, the patient answered questions to Sections 1 and 2. Using the substeps shown in FIG. 3, data analysis of step 104 is performed. In substep 300, the raw nociceptive pain score 304 is calculated by summing the answer values in the nociceptive pain category 216, and the raw neuropathic pain score 308 is calculated by summing the answer values in the neuropathic pain category 220. For the answers given in Example #1, the raw nociceptive pain score (RnocPS) 304=12, and the raw neuropathic pain score (RneuPS) 308=35.

In substep 312 the partial nociceptive pain score (PnocPS) 316 and the partial neuropathic pain score (PneuPS) 320 are calculated. Since the patient answered questions 200 in Sections 1 and 2 (upper extremity pain) the equations for calculating the partial nociceptive pain score (PnocPS) 316 and the partial neuropathic pain score (PneuPS) 320 are Equations 5 and 6 as follows, where the multipliers are taken from Table 1:

$$PnocPS = 0.4761 \times 12 \text{ thus, } PnocPS = 5.7, \text{ and} \qquad \text{Equation 5}$$

$$PneuPS = 0.196 \times 35 \text{ thus } PneuPS = 6.9 \qquad \text{Equation 6}$$

After calculating the partial nociceptive pain score (PnocPS) 316 and the partial neuropathic pain score (PneuPS) 320, the next substep 324 of the data analysis 104 is to calculate the final nociceptive pain score (FnocPS) 328 and the final neuropathic pain score (FneuPS) 332 using Conditions 1-9. In the present example, three of Conditions 1-9 are met. That is, for Condition #4, since S1Q2=b, c, or d and S1Q5=c, 1.5 points are added the partial neuropathic pain score (PneuPS) 320; for Condition #7, since S1Q9 has two or more answers of a through g, 5 points are added to the partial neuropathic pain score (PneuPS) 320; and for Condition #9, since S2Q3=b, 1 point is added to the partial neuropathic pain score (PneuPS) 320.

Thus, $$FnocPS = PnocPS = 5.7, \text{ and}$$

$$FneuPS = PneuPS + AP$$

$$FneuPS = PneuPS + 1.5 + 5 + 1$$

$$FneuPS = 6.9 + 1.5 + 5 + 1 = 14.4 \qquad \text{Equation 22}$$

After calculating the final nociceptive pain score (FnocPS) 328 and the final neuropathic pain score (FneuPS) 332, the next substep 336 of the data analysis 104 is to calculate the final ratio 340 at step 336, where the final ratio 340 is final neuropathic pain score (FneuPS) 332 divided by the final nociceptive pain score (FnocPS) 328.

$$\text{Final Ratio} = \frac{FneuPS}{FnocPS} \text{ or} \qquad \text{Equation 23}$$

$$\text{Final Ratio} = \frac{14.4}{5.7}$$

$$\text{Final Ratio} = 2.5$$

Since the final ratio 340 has a value of 2.5 which is greater than 2, there is a strong possibility that the pain is neuropathic, and the treating physician should undertake a course of treatment directed at treating neuropathic pain and not nociceptive pain. Thus, for example, the treating physician may undertake to use neurostimulation to treat the patient's pain.

EXAMPLE #2

In accordance with FIG. 1A, the first step 100 is to gather information per the questions listed in Sections 1-5 of FIGS. 2A-2E. For these questions, the patient answered questions 200 in Sections 1 and 3 as follows:

Section 1

As seen above, in Example #2 the patient answered questions to Sections 1 and 3. Using the substeps shown in FIG. 3, data analysis of step 104 is performed. In substep 300, the raw nociceptive pain score 304 is calculated by summing the answer values in the nociceptive pain category 216, and the raw neuropathic pain score 308 is calculated by summing the answer values in the neuropathic pain category 220. For the answers given in Example #2, the raw nociceptive pain score (RnocPS) 304=16, and the raw neuropathic pain score (RneuPS) 308=10.

In substep 312 the partial nociceptive pain score (PnocPS) 316 and the partial neuropathic pain score (PneuPS) 320 are calculated. Since the patient answered questions 200 in Sections 1 and 3 (lower extremity pain) the equations for calculating the partial nociceptive pain score (PnocPS) 316 and the partial neuropathic pain score (PneuPS) 320 are Equations 7 and 8 as follows, where the multipliers are taken from Table 1:

$$PnocPS = 0.5263 \times 16 \text{ thus, } PnocPS = 8.4, \text{and} \qquad \text{Equation 7}$$

$$PneuPS = 0.2272 \times 10 \text{ thus } PneuPS = 2.3 \qquad \text{Equation 8}$$

After calculating the partial nociceptive pain score (PnocPS) 316 and the partial neuropathic pain score (PneuPS) 320, the next substep 324 of the data analysis 104 is to calculate the final nociceptive pain score (FnocPS) 328 and the final neuropathic pain score (FneuPS) 332 using Conditions 1-9, In the present example, none of Conditions 1-9 are met.

Thus, $$FnocPS = PnocPS = 8.4, \text{and}$$

$$FneuPS = PneuPS = 2.3$$

GENERAL QUESTIONS FOR ALL PATIENTS

| Question Designation 204 | Question 200 | Answer Designation 212 | Answer 208 | Nociceptive Pain Category 216 | Neuropathic Pain Category 220 |
|---|---|---|---|---|---|
| S1Q1 | How frequent is your pain? | c | Not constant: every day infrequently | 4 | 1 |
| S1Q2 | How long have you had the pain? | b | 1-6 months | 2 | 2 |
| S1Q3 | How bad is the pain? (at its worst) | c | Moderate | 2 | 1 |
| S1Q4 | How bad is the pain? (at its least) | d | Mild | 4 | 1 |
| S1Q5 | About burning pain, which one applies to you? | a | I don't have any | 0 | 0 |
| S1Q6 | How is your pain at night? (for time 1 to 6 months) | b | Much less than during the day | 2 | 1 |
| S1Q7 | Does your pain wake you up at night? (for time 1 to 6 months) | b | Seldom | 2 | 1 |
| S1Q8 | Are you numb in the area of worst pain? | b | No | 0 | 0 |
| S1Q9 | Do you have any of the following in the pain area? (choose all that apply) | a | Swelling | 0 | 1 (if time is >1 month) |

Section 3

| Question Designation 204 | Question 200 | Answer Designation 212 | Answer 208 | Nociceptive Pain Category 216 | Neuropathic Pain Category 220 |
|---|---|---|---|---|---|
| | FOR PATIENTS WITH LOWER EXTREMITY PAIN | | | | |
| S3Q1 | Do your legs ever give out on you? | b | No | 0 | 0 |
| S3Q2 | Is your leg swollen even when you lie flat? | a | Yes | 0 | 1 |
| S3Q3 | Do you have problems voiding? | a | Yes | 0 | 1 |
| S3Q4 | How long have you had problems voiding? | a | <6 months | 0 | 0 |

After calculating the final nociceptive pain score (FnocPS) 328 and the final neuropathic pain score (FneuPS) 332, the next substep 336 of the data analysis 104 is to calculate the final ratio 340 at step 336, where the final ratio 340 is final neuropathic pain score (FneuPS) 332 divided by the final nociceptive pain score (FnocPS) 328.

$$\text{Final Ratio} = \frac{FneuPS}{FnocPS} \text{ or} \qquad \text{Equation 23}$$

$$\text{Final Ratio} = \frac{2.3}{8.4}$$

$$\text{Final Ratio} = 0.28$$

Since the final ratio 340 has a value of 0.28, which is less than 1, there is a strong possibility that the pain is nociceptive, and the treating physician should undertake a course of treatment directed at treating nociceptive pain and not neuropathic pain. Thus, for example, the treating physician may undertake to use physical therapy or surgery of an injury site to treat the patient's pain.

EXAMPLE #3

In accordance with FIG. 1A, the first step 100 is to gather information per the questions listed in Sections 1-5 of FIGS. 2A-2E. In Example #3, the patient answered questions to Sections 1, 3, and 5 as follows:

Section 1

| | GENERAL QUESTIONS FOR ALL PATIENTS | | | | Nociceptive Pain Category 216 | Neuropathic Pain Category 220 |
|---|---|---|---|---|---|---|
| Question Designation 204 | Question 200 | Answer Designation 212 | Answer 208 | | | |
| S1Q1 | How frequent is your pain? | c | Not constant: every day infrequently | | 4 | 1 |
| S1Q2 | How long have you had the pain? | d | More than 1 year | | 1 | 4 |
| S1Q3 | How bad is the pain? (at its worst) | b | Severe | | 3 | 3 |
| S1Q4 | How bad is the pain? (at its least) | d | Mild | | 4 | 1 |
| S1Q5 | About burning pain, which one applies to you? | b | It is a small part of my pain | | 0 | 4 |
| S1Q6 | How is your pain at night? (for time >6 months) | b | Much less than during the day | | 3 | 1 |
| S1Q7 | Does your pain wake you up at night? (for time >6 months) | b | Seldom | | 2 | 1 |
| S1Q8 | Are you numb in the area of worst pain? | b | No | | 0 | 0 |
| S1Q9 | Do you have any of the following in the pain area? (choose all that apply) | a | Swelling | | 0 | 1 (if time is >1 month) |

Section 3

| | FOR PATIENTS WITH LOWER EXTREMITY PAIN | | | Nociceptive Pain Category 216 | Neuropathic Pain Category 220 |
|---|---|---|---|---|---|
| Question Designation 204 | Question 200 | Answer Designation 212 | Answer 208 | | |
| S3Q1 | Do your legs ever give out on you? | b | No | 0 | 0 |
| S3Q2 | Is your leg swollen even when you lie flat? | a | Yes | 0 | 1 |
| S3Q3 | Do you have problems voiding? | a | Yes | 0 | 1 |
| S3Q4 | How long have you had problems voiding? | a | <6 months | 0 | 0 |

Section 5

| | FOR PATIENTS WHO HAVE HAD PREVIOUS SPINE SURGERY | | | Nociceptive Pain Category 216 | Neuropathic Pain Category 220 |
|---|---|---|---|---|---|
| Question Designation 204 | Question 200 | Answer Designation 212 | Answer 208 | | |
| S5Q1 | How many spine surgeries have you had? (related to the existing pain problem) | c | >2 | 0 | 2 |

| | FOR PATIENTS WHO HAVE HAD PREVIOUS SPINE SURGERY | | | Nociceptive | Neuropathic |
|---|---|---|---|---|---|
| Question Designation 204 | Question 200 | Answer Designation 212 | Answer 208 | Pain Category 216 | Pain Category 220 |
| S5Q2 | Did any of the spine surgeries ever help you with your neck/back pain? | c | No | 0 | 1 |
| S5Q3 | Did any of the spine surgeries ever help you with your arm(s)/leg(s) pain? | c | No | 0 | 1 |
| S5Q4 | Was your arm/leg pain made permanently worse after one of the spine surgeries? | a | Yes | 0 | 1 |

Using the substeps shown in FIG. 3, data analysis of step 104 is performed. In substep 300, the raw nociceptive pain score 304 is calculated by summing the answer values in the nociceptive pain category 216, and the raw neuropathic pain score 308 is calculated by summing the answer values in the neuropathic pain category 220. For the answers given in Example #3, the raw nociceptive pain score (RnocPS) 304=17, and the raw neuropathic pain score (RneuPS) 308=23.

In substep 312 the partial nociceptive pain score (PnocPS) 316 and the partial neuropathic pain score (PneuPS) 320 are calculated. Since the patient answered questions 200 in Sections 1, 3 and 5 (lower extremity pain and spine surgery) the equations for calculating the partial nociceptive pain score (PnocPS) 316 and the partial neuropathic pain score (PneuPS) 320 are Equations 19 and 20 as follows, where the multipliers are taken from Table 1:

$$PnocPS = 0.4761 \times 17 \text{ thus, } PnocPS = 8.1, \text{ and} \quad \text{Equation 19}$$

$$PneuPS = 0.204 \times 23 \text{ thus } PneuPS = 4.7 \quad \text{Equation 20}$$

After calculating the partial nociceptive pain score (PnocPS) 316 and the partial neuropathic pain score (PneuPS) 320, the next substep 324 of the data analysis 104 is to calculate the final nociceptive pain score (FnocPS) 328 and the final neuropathic pain score (FneuPS) 332 using Conditions #1-9. In the present example, Condition #5 is met because S1Q2=b, c, or d and S1Q5=b, thus, 1 point is added to the partial neuropathic pain score (PneuPS) 320.

Thus, $$FnocPS = PnocPS = 8.1, \text{ and}$$

$$FneuPS = PneuPS + 1 = 5.7$$

After calculating the final nociceptive pain score (FnocPS) 328 and the final neuropathic pain score (FneuPS) 332, the next substep 336 of the data analysis 104 is to calculate the final ratio 340 at step 336, where the final ratio 340 is the final neuropathic pain score (FneuPS) 332 divided by the final nociceptive pain score (FnocPS) 328.

$$\text{Final Ratio} = \frac{FneuPS}{FnocPS} \text{ or} \quad \text{Equation 23}$$

$$\text{Final Ratio} = \frac{5.7}{8.1}$$

$$\text{Final Ratio} = 0.70$$

Since the final ratio 340 has a value of 0.70, which is less than 1, there is a strong possibility that the pain is nociceptive, and the treating physician should undertake a course of treatment directed at treating nociceptive pain and not neuropathic pain.

Referring again to FIG. 1A, as discussed above, in step 100 data is gathered to provide information regarding the patient's pain. The information may be gathered on paper, or a computing device may be used. In addition, subsequent analysis may also be conducted without using a computer. However, a preferred embodiment utilizes a computer because of the ease of use, and because a computer can also facilitate electronic storage of the data, analysis of the data, transmission of the data, etc. The computer may also be interconnected to a network, wherein various storage and/or computational steps are conducted on a different computing device and/or database, such as a server, that is in communication with the computing device being used by the patient or physician. The following paragraphs discuss these embodiments.

Figure 4:
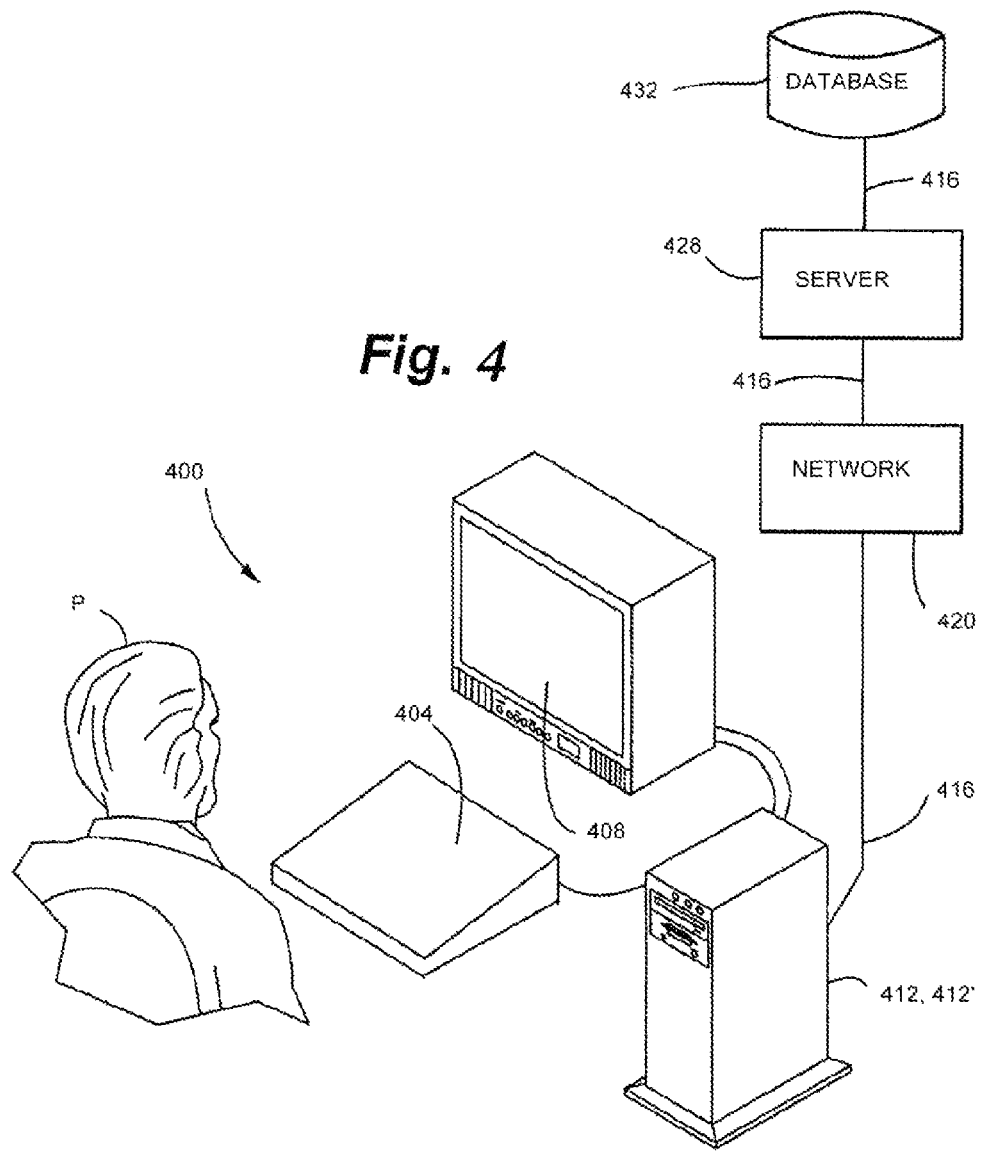
FIG. 4 is a pain analysis system according to an embodiment of the present invention.

Referring now to FIG. 1B, in step 112, data storage may be performed concurrently with the patient answering questions 200. More particularly, the patient utilizes an interactive program to read and answer the questions 200 shown on FIGS. 2A-2E. Referring now to FIG. 4, the patient P is shown using a pain analysis system 400. The pain analysis system 400 includes a data entry or input device, such as a keyboard 404, and an output device for displaying the questions 200 and the answers 208, such as display 408. As those skilled in the art will appreciate, the keyboard and display may be combined into a touch screen. For the system 400 shown in FIG. 4, a computer 412 is in communication with the keyboard 404 and the display 408. The computer 412 may be a personal computer, or alternatively, the computer 412 may be a laptop computer, handheld computer, such as a PDA, or other similar device known to those skilled in the art.

The software for displaying the questions 200 shown in FIGS. 2A-2E may be resident on the computer 412, or loaded onto the computer 412 over a data network 420 accessed by a network connection or communication link 416 (e.g., USB, Ethernet, wireless, etc.). Embodiments both with and without a network element are described below.

Figure 5:
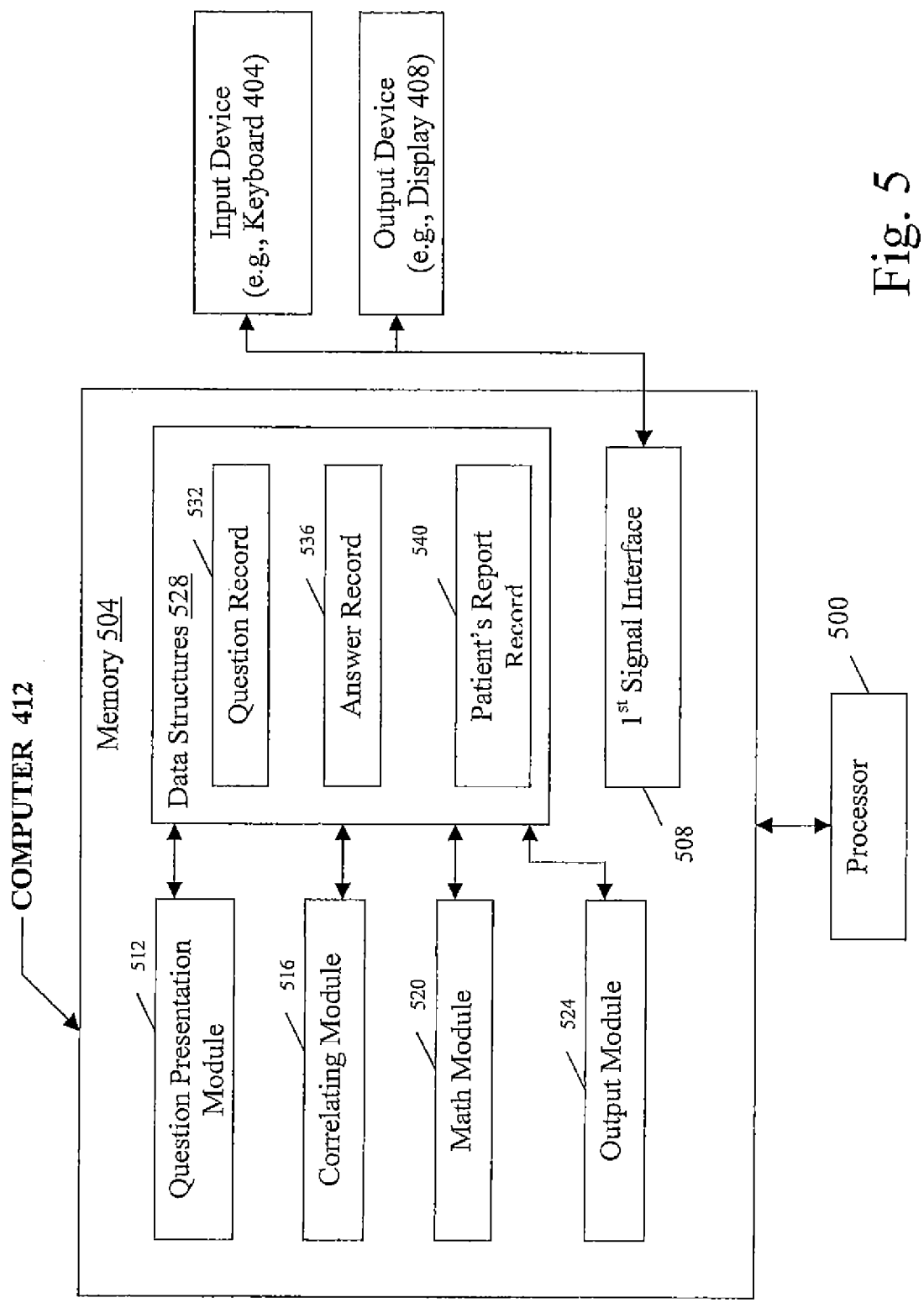
FIG. 5 is a block diagram of a computer in accordance with embodiments of the present invention.

Referring now to FIG. 5, a block diagram of components and features of the computer 412 is shown for an embodiment for implementing part of the pain analysis system 400, wherein the computer 412 is not interconnected to a network. Here, the computer 412 includes a number of modules for the data-gathering step 100, the data analysis step 104, and the pain prediction step 108. As shown in FIG. 5, the computer 412 includes a processor 500, a memory 504 and a first signaling interface 508 operable to communicate with the input device, such as a keyboard 404, and an output device, such as the display 408. The memory 504 includes a plurality of stored program applications or modules that implement various features of the pain analysis system 400. In accordance with embodiments of the present invention, the memory 504 may include a question presentation module 512, a correlating module 516, a math module 520, and an output module 524. Additionally, the memory 504 may include data structures 528 associated with the various modules. In accordance with embodiments of the present invention, the data structures 528 include a question record 532, an answer record 536, and a patient report record 540. The operation of the various modules and data structures is described in greater detail below.

The question presentation module 512 operates to present questions 200 to the patient, physician or medical staff member. The question presentation module 512 may also access an updated question record 532 for obtaining the latest questions for presentation to the patient P. The question presentation module 512 also keeps an answer record 536 of the responses given by the patient.

The correlating module 516 operates to correlate the answers in the answer record 536 to the assigned numerical values in the nociceptive pain category 216 and the neuropathic pain category 220.

The math module 520 conducts step 104 of the data analysis, including: (a) substep 300 of summing the numerical values within the nociceptive pain category 216 to determine a raw nociceptive pain score 304, and summing the numerical values within the neuropathic pain category 220 to determine a raw neuropathic pain score 308; (b) substep 312 of multiplying the raw nociceptive pain score 304 by a first multiplier to determine a partial nociceptive pain score 316, and multiplying the raw neuropathic pain score 308 by a second multiplier to determine a partial neuropathic pain score 320; (c) substep 324 of checking whether any of Conditions #1-9 are met and, if so, adding appropriate points to the partial nociceptive pain score 316 to obtain the final nociceptive pain score 328, and adding appropriate points to the partial neuropathic pain score 320 to obtain the final neuropathic pain score 332; (d) substep 336 of dividing the final neuropathic pain score 332 by the final nociceptive pain score 328 to determine a final ratio 340; and (e) comparing the final ratio 340 with a standard for assessing whether the patient is suffering from nociceptive pain and/or neuropathic pain.

The output module 524 prepares a patient report record 540 that may include a patient identifier, the questions 200, question designations 204, answers designations 212 and answers 208, together with the final ratio 340 and a prediction as to whether the patient's pain is nociceptive pain, neuropathic pain, or a combination of both nociceptive and neuropathic pain. An example of a patient report 600 prepared from the patient report record 540 by the output module 524 is provided as FIG. 6. In accordance with embodiments of the present invention, the patient report 600 preferably includes a number of fields of information that may comprise a patient identifier 604, the questions 200, question designations 204, answers designations 212, answers 208, the raw nociceptive pain score 304, raw neuropathic pain score 308, partial nociceptive pain score 316, partial neuropathic pain score 320, final nociceptive pain score 328, final neuropathic pain score 332, final ratio 340, and a pain prediction 608 as to whether the patient's pain is nociceptive pain, neuropathic pain, or a combination of both nociceptive and neuropathic pain.

Referring again to FIG. 1B, and in accordance with at least one embodiment of the invention, at decision diamond 116, if the computer is interconnected to a server 428 or general purpose computer the patient's data and answers may be uploaded. Then at step 124 the data from the computer 412' is transmitted to the server 428, wherein the server 428 conducts one or more aspects of the method of the invention. That is, the server 428 may include software for interacting with the patient P (or the patient's physician/medical staff), and the server 428 may also include memory for storing the questions 200 and the answer designations 212 for the answers submitted by the patient P. For this embodiment, the computer 412' may be interconnected to a data network 420 by a network connection 416, such as an Ethernet connection. If the server 428 is located remotely from the computer 412', the network connection 416 may include components, such as a gateway (not shown), to provide access to a distributed data network, such as the Internet. At step 128, the data is analyzed consistent with the data analysis of step 104 described above.

The exemplary systems and methods of this invention will be described in relation to distributed processing networks. However, to avoid unnecessarily obscuring the present invention, the following description omits a number of known structures and devices. This omission is not to be construed as a limitation of the scope of the claimed invention. Specific details are set forth to provide an understanding of the present invention. It should, however, be appreciated that the present invention may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, or collocated on a particular node of a distributed network, such as an analog and/or digital telecommunications network, a packet-switched network, or a circuit-switched network. It will be appreciated from the following description, and for reasons of computational efficiency, that the components of the system can be arranged at any location within a distributed network of components without affecting the operation of the system. For example, the various components can be located in a switch, media server, gateway, at one or more users' premises, or some combination thereof.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Figure 7:
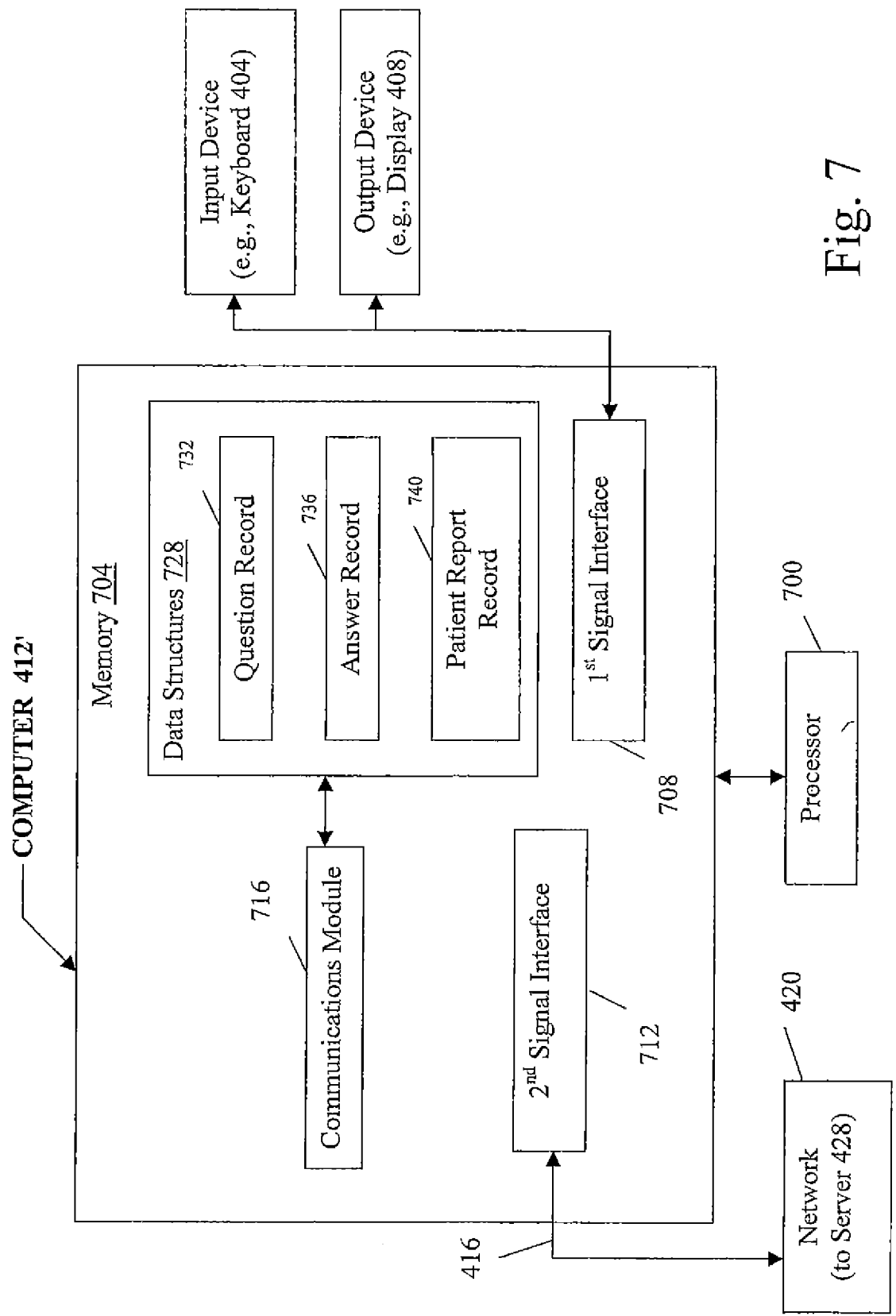
FIG. 7 is another block diagram of a computer in accordance with embodiments of the present invention.

Referring now to FIG. 7, a block diagram of components and features of the computer 412' is shown for an embodiment wherein the computer 412' is interconnected to a network 420 for implementing part of the pain analysis system 400. Here, the computer 412' includes a processor 700, a memory 704 and a first and second signaling interfaces 708 and 712. The first signal interface 708 is operable to communicate with the input device, such as a keyboard 404, and an output device, such as the display 408. The second signal interface 712 operates to communicate with a network 420 over communication link 416 to communicate with a server 428 or a general-purpose network computer.

The memory 704 may include a plurality of stored program applications or modules that implement various features of a pain analysis system 400. In accordance with embodiments of the present invention, the memory 704 includes a communication module 716 for assisting with communications between the computer 412' and the network 420 that is linked to the server 428. Additionally, the memory 704 may include data structures 728 for locally storing information in case of a communication disruption over the network 420, where such information may include a question record 732, an answer record 736, and a patient report record 740.

Figure 8:
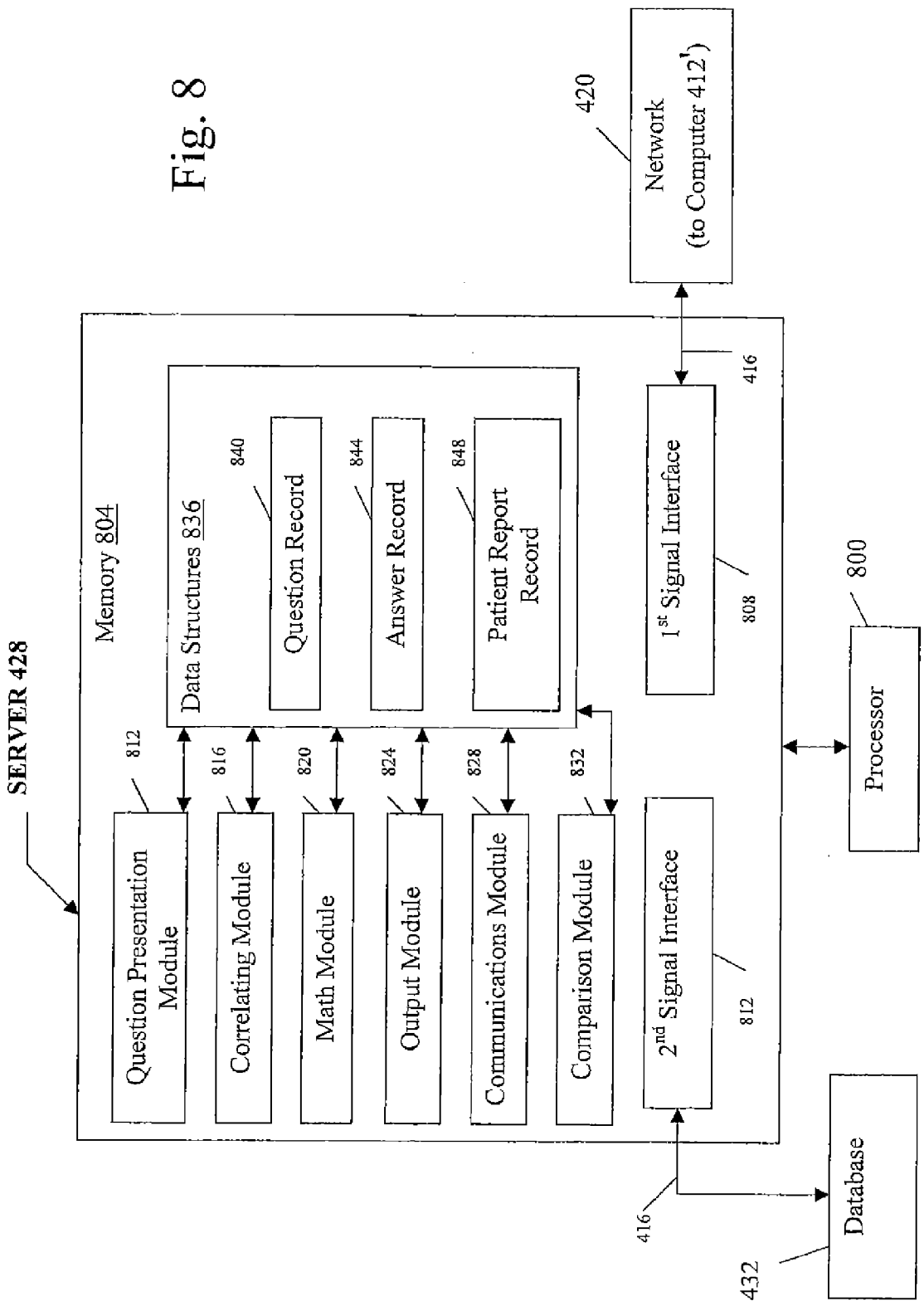
FIG. 8 is a block diagram of a server in accordance with embodiments of the present invention.

Referring now to FIG. 8, a block diagram of components and features of the server 428 is shown for an embodiment where a computer, such as the computer 412' shown in FIG. 7, is interconnected to a network 420 and sever 428 for implementing part of the pain analysis system 400. The data network 420 can be any circuit- or packet-switched network, with a packet-switched network, such as the Internet or World Wide Web, being preferred. The patient information from the questions 200 shown in FIGS. 2A-2E may be converted into a selected form, packetized, and transmitted over the network 420. The form of the information can be in accordance with any selected language, such as the eXtensible Markup Language or XML, the HyperText Markup Language or HTML, Remote Method Invocation or RMI, or Direct Socket Connections. The packets can be transported using any suitable protocol, such as the Transport Control Protocol/Internet Protocol suite of protocols, Simple Object Access Protocol, or User Datagram Protocol.

Referring still to FIG. 8, the server 428 includes a processor 800, a memory 804, and first and second signaling interfaces 808 and 812. The first signal interface 808 operates to communicate with a network 420 over communication link 416 to communicate with the computer, such as the computer 412' of FIG. 7. The second signal interface 812 is operable to communicate with a database 432 over a communication link 416. The memory 804 includes a plurality of stored program applications or modules that implement various features of a pain analysis system 400. In accordance with embodiments of the present invention, the memory 804 may include a question presentation module 812 similar to question presentation module 512 described above, a correlating module 816 similar to correlating module 516 described above, a math module 820 similar to math module 520 described above, an output module 824 similar to output module 524 described above, and a communications module 828 for assisting with communications between the server 428 and the network 420 that is linked to the computer 412'. In addition, the memory 804 may include a comparison module 832 as described below. Additionally, the memory 804 may include data structures 836 associated with the various modules. In accordance with embodiments of the present invention, the data structures 836 include a question record 840, an answer record 844, and a patient report record 848, where such records are similar to the data structures described above, namely, question record 532, answer record 536, and the patient report record 540, respectively.

Referring again to FIG. 1B, the method may also include step 132, wherein a comparison is performed of the patient's answers and data analysis results against those of prior case studies and/or from other patients, such a patients from a pool of participating physicians. That is, if used, in step 132 the server 428 operates in accordance with comparison module 832 that compares data from the patient's answers against those of prior cases, including patients that previously responded similarly, where such prior data is stored in database 432. The comparison module 832 may consider treatment successes of the prior cases and provide recommendations for treatment and/or the probability of successful treatment for the subject patient based upon comparison with the prior cases. In step 134, the results of the analysis, including any comparison information (if performed) is transmitted back to the treating physician. Alternatively, raw data may be provided to a comparison module (not shown) that is run locally on the computer 412'. Accordingly, in it at least one embodiment of the invention, a system is provided that allows the physician using a networked computer 412' to tap into database 432 that includes additional patient data to supplement data normally available to the treating physician.

Similar to output module 524 described above, the output module 824 prepares a patient report record 848. An example of a patient report 900 prepared from the patient report record 848 by the output module 824 is provided as FIG. 9. In accordance with embodiments of the present invention, the patient report 900 preferably includes the fields shown in FIG. 6, and may further include comparison data 904. For the exemplary comparison data 904 shown in FIG. 9, the top three matches of the subject patient having patient identifier 604 "Jane Doe," is compared against anonymous patients #1-3. As shown in FIG. 9, the comparison module 828 preferably provides information through the output module 824 that includes the percent (%) answer match with the comparison patient, as well as other relevant data, such as the final ratio 340 of the comparison patient, the treatment type for the comparison patient (e.g., neurostimulation), and the comparison patient's description of the treatment effectiveness (e.g., good). Here, the physician treating a particular patient P can obtain information that not only identifies the nature of the patient's pain, but further compares the patient against information in the database 432 for similar answers so that the physician can obtain a measure of how effective a course of treatment may be for the subject patient relative to patients experiencing the same type of pain.

While the flowcharts have been discussed and illustrated in relation to a particular sequence of events, it should be appreciated that changes, additions, and omissions to this sequence can occur without materially affecting the operation of the invention.

All publications, patents and patent applications mentioned in this specification are herein incorporated in their entirety by reference into the specification, to the same extent as if each individual publication, patent or patent application was specifically and individually indicated to be incorporated herein by reference, except insofar as the subject matter may conflict with that of the present invention (in which case what is present herein shall prevail). In addition, citation or identification of any reference in this application shall not be construed as an admission that such reference is available as "prior art" to the present invention. Furthermore, notwithstanding any other wording herein, nothing herein will be construed as an admission of "prior art."

While particular embodiments of the present invention have been described in some detail, it should be understood that other related embodiments are intended to be within the scope of the present invention, whether such other related embodiments include other features that are well within the knowledge of those of ordinary skill in this art, and/or whether such features use conventional structures or those that may be developed in the future.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field," such claims should not be limited by the language chosen under this heading to describe the so-called field. Further, a description of a technology in the "Background" is not to be construed as an admission that technology is prior art to any invention(s) in this disclosure. Neither is the "Summary" to be considered as a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A method of distinguishing nociceptive pain from neuropathic pain in a patient, comprising:
   (a) providing a plurality of questions wherein at least a first question and a second question of the plurality of questions are directed to aspects of pain experienced by the patient, wherein each of the first question and the second question have at least one corresponding answer;
   (b) obtaining at least one answer to the first question and at least one answer to the second question;
   (c) correlating at least two numerical values to each answer of the first question, and correlating at least two numerical values to each answer of the second question, a first numerical value of the two numerical values corresponding to a nociceptive pain category and a second numerical value of the two numerical values corresponding to a neuropathic pain category;
   (d) summing the numerical values within the nociceptive pain category to determine a raw nociceptive pain score, and summing the numerical values within the neuropathic pain category to determine a raw neuropathic pain score;
   (e) multiplying the raw nociceptive pain score by a first multiplier to determine a partial nociceptive pain score, and multiplying the raw neuropathic pain score by a second multiplier to determine a partial neuropathic pain score;
   (f) dividing the partial neuropathic pain score by the partial nociceptive pain score to determine a final ratio; and
   (g) comparing the final ratio with a standard for assessing whether the patient is suffering from nociceptive pain and/or neuropathic pain;
   wherein one or more of said providing, obtaining, correlating, summing, multiplying, and dividing steps are performed on a computation device.

2. The method of claim 1, wherein the questions are substantially directed to at least one of nociceptive pain indicators and neuropathic pain indicators.

3. The method of claim 1, wherein the questions are directed to one or more of (a) upper extremity pain, (b) lower extremity pain, (c) surgery other than spine surgery, and (d) spine surgery.

4. The method of claim 1, further comprising checking at least one answer prior to the dividing step, wherein if the answer meets a first condition, then a mathematical adjustment is made to one or more of the partial nociceptive pain score and the partial neuropathic pain score prior to the dividing step.

5. The method of claim 1, wherein one or more of said providing, obtaining, correlating, summing, multiplying, and dividing steps are performed using a server interconnected to a network.

6. The method of claim 5, further comprising providing a recommendation for treatment of the patient.

7. The method of claim 5, further comprising comparing one or more of the answers to the plurality of questions to a database.

8. The method of claim 7, further comprising providing a recommendation for treatment of the patient.

9. The method of claim 5, further comprising comparing the final ratio to a database.

10. The method of claim 9, further comprising comparing one or more of the answers to the plurality of questions to a database.

11. The method of claim 10, further comprising providing a recommendation for treatment of the patient.

12. A system for distinguishing nociceptive pain from neuropathic pain in a patient, comprising:
   a computer device including:
      a memory including a question access module, the question access module operable to access a listing of a plurality of questions wherein at least a first question and a second question of the plurality of questions are directed to aspects of pain experienced by the patient, wherein each of the first question and the second question have at least one corresponding answer;
      a display operable to display the plurality of questions; and
      an input device operable to receive at least one answer to the first question and at least one answer to the second question;
      wherein the memory includes a correlating module operable to correlate at least two numerical values to each answer of the first question, and correlate at least two numerical values to each answer of the second question, a first numerical value of the two numerical values corresponding to a nociceptive pain category and a second numerical value of the two numerical values corresponding to a neuropathic pain category;
      wherein the memory includes a math module operable to:
         (a) sum the numerical values with the nociceptive pain category to determine a raw nociceptive pain score, and sum the numerical values within the neuropathic pain category to determine a raw neuropathic pain score;

(b) multiply the raw nociceptive score by a first multiplier to determine a partial nociceptive pain score, and multiply the raw neuropathic pain score by a second multiplier to determine a partial neuropathic pain score;

(c) divide the partial neuropathic pain score by the partial nociceptive pain score to determine a final ratio; and (d) compare the final ratio with a standard to assess whether the patient is suffering from nociceptive pain and/or neuropathic pain;

the memory including an output module operable to generate an output including a predictive indicator as to whether the patient is suffering from nociceptive pain and/or neuropathic pain.

13. The system of claim 12, further comprising a database of information operatively associated with the computer, the database including a plurality of answers of a second patient.

14. The system of claim 13, wherein the memory comprises a comparison module in communication with the database and operable to compare the patient's at least one answer to the first question and the at least one answer to the second question to a corresponding answer to the first question and a corresponding answer to the second question of the second patient.

15. The system of claim 12, wherein the memory includes a checking module operable to check at least one answer and mathematically adjust one or more of the partial nociceptive pain score and the partial neuropathic pain score.

16. A method of distinguishing nociceptive pain from neuropathic pain in a patient, comprising:

(a) providing at least a first question and a second question directed to aspects of pain experienced by the patient, wherein each of the first and second questions have at least one corresponding answer;

(b) obtaining at least one answer to the first and second questions;

(c) correlating at least two numerical values to at least one of the answers to the first and second questions, a first numerical value of the two numerical values corresponding to a nociceptive pain category and a second numerical value of the two numerical values corresponding to a neuropathic pain category; and (d) performing a plurality of mathematical steps including summing the values in the nociceptive and neuropathic pain categories to obtain a pair of resultants, multiplying the pair of resultants by at least one coefficient to obtain a pair of modified resultants, and then dividing at least one of the modified resultants by the other to obtain a final resultant;

wherein a relative value of the final resultant is indicative of one or more of nociceptive pain and neuropathic pain; and wherein one or more of said providing, obtaining, correlating, summing, multiplying, and dividing steps are performed on a computation device.

17. The method of claim 16, wherein one or more of said providing, obtaining, correlating, and performing steps are conducted using a server interconnected to a network.

18. The method of claim 17, further comprising comparing one or more of the answers to the plurality of questions to a database and providing a recommendation for treatment of the patient.

* * * * *